United States Patent
Aube et al.

(10) Patent No.: US 10,118,896 B2
(45) Date of Patent: Nov. 6, 2018

(54) ANTAGONISTS OF THE KAPPA OPIOID RECEPTOR

(71) Applicant: University of Kansas, Lawrence, KS (US)

(72) Inventors: Jeffrey Aube, Lawrence, KS (US); Kevin Frankowski, Lawrence, KS (US); Thomas Prisinzano, Lawrence, KS (US); Laura Bohn, Jupiter, FL (US)

(73) Assignees: UNIVERSITY OF KANSAS, Lawrence, KS (US); THE SCRIPPS RESEARCH INSTITUTE, La Jolla, CA (US)

( * ) Notice: Subject to any disclaimer, the term of this patent is extended or adjusted under 35 U.S.C. 154(b) by 20 days.

(21) Appl. No.: 15/529,290

(22) PCT Filed: Nov. 25, 2015

(86) PCT No.: PCT/US2015/062708
§ 371 (c)(1),
(2) Date: May 24, 2017

(87) PCT Pub. No.: WO2016/086149
PCT Pub. Date: Jun. 2, 2016

(65) Prior Publication Data
US 2017/0260141 A1    Sep. 14, 2017

Related U.S. Application Data

(60) Provisional application No. 62/084,932, filed on Nov. 26, 2014.

(51) Int. Cl.
C07D 217/08    (2006.01)
C07D 209/44    (2006.01)
C07D 223/16    (2006.01)

(52) U.S. Cl.
CPC ......... *C07D 217/08* (2013.01); *C07D 209/44* (2013.01); *C07D 223/16* (2013.01)

(58) Field of Classification Search
None
See application file for complete search history.

(56) References Cited

U.S. PATENT DOCUMENTS 5,672,662 A    9/1997    Harris et al.
2014/0243333 A1    8/2014    Aube et al.

FOREIGN PATENT DOCUMENTS

WO    WO-2013/040321 A1    3/2013

OTHER PUBLICATIONS

Birch, PJ. et al. Norbinaltorphimine: antagonist profile at kappa opioid receptors. Eur. J. Pharmacol, 1987, abstract.*
Lamberts, T. et al. Opioid Receptor Interacting Proteins and the Control of Opioid Signaling. Current Pharmaceutical Design, 2013, abstract.*
Carlezon, WA. et al. Kappa-opioid ligands in the study and treatment of mood disorders. Pharmacology & Therapeutics, 2009, p. 334.*
Zhong, M. et al. Discovery of tetrahydroisoquinoline (THIQ) derivatives as potent and orally bioavailable LFA-1/ICAM-1 antagonists. Bioorganic & Medicinal Chemistry Letters, 2010, p. 5271.*
Carr, GV. et al. Antidepressant-Like Effects of kappa-Opioid Receptor Antagonists in Wistar Kyoto Rats. Neuropsychopharmacology, 2010, p. 761.*
Carroll et al, Development of k Opioid Receptor Agonists, J. Med.Chem., 56, 2013, 2178-2195.
"Substance Record for SID 93575678" to PubChem (https://pubchem.ncbi.nlm.nih.gov/substance/93575678; retrieved on Oct. 9, 2017).
Bohn LM, Lefkowitz RJ, Caron MG. Differential Mechanisms of Morphine Antinociceptive Tolerance Revealed in (beta)Arrestin-2 Knock-Out Mice. J Neurosci. 2002, 22(23): 10494-10500.
Bohn, L.M., Gainetdinov, R.R., Sotnikova, T.D., Medvedev, I.O., Lefkowitz, R.J., Dykstra, L.A., Caron, M.G. Enhanced Rewarding Properties of Morphine, but not Cocaine, in beta(Arrestin)-2 Knock-Out Mice. The Journal of Neuroscience : the Official Journal of the Society for Neuroscience, 2003, 23(32): 10265-10273.
Bohn, L.M., Xu, F., Gainetdinov, R.R., Caron, M.G. Potentiated Opioid Analgesia in Norepinephrine Transporter Knock-Out Mice. The Journal of Neuroscience: the Official Journal of the Society for Neuroscience, 2000, 20(24):9040-9045.
Frankowsi et al. Potency enhancement of the kappa-opioid receptor antagonist probe ML140 through sulfonamide constraint utilizing a tetrahydroisoquinoline motif. Bioorg. Med. Chem. 23 2015, 3948-3956.
International Search Report and Written Opinion in PCT/US2015/062708, dated Feb. 5, 2016 (7 pages).
Kreibich, A.S., Blendy, J.A. cAMP Response Element-Binding Protein Is Required for Stress But Not Cocaine-Induced Reinstatement. J Neurosci. 2004, 24(30):6686-6692.
Medvedev, I.O., Gainetdinov, R.R., Sotnikova, T.D., Bohn, L.M., Caron, M.G., Dykstra, L.A. Characterization of conditioned place preference to cocaine in congenic dopamine transporter knockout female mice. Psychopharmacology. 2005;180(3):408-13.
Morgenweck, J., Frankowski, K.J., Prisinzano, T.E., Aube, J., Bohn, L.M. Investigation of the role of ~arrestin2 in kappa opioid receptor modulation in a mouse model of pruritus. Neuropharmacology, 2015, 99:600-609.
Patkar, K.A.; Wu, J.; Ganno, M.L.; Singh, H.D.; Ross, N.C.; Rasakham, K.; Toll, L.; McLaughlin, J.P. Physical Presence of Nor-Binaltorphimine in Mouse Brain over 21 Days after a Single Administration Corresponds to Its Long-Lasting Antagonistic Effect on kappa-Opioid Receptors. J Pharmacol. Exp. Ther. 2013, 346, 545-554.

(Continued)

Primary Examiner — Noble E Jarrell
(74) Attorney, Agent, or Firm — Foley & Lardner LLP

(57) ABSTRACT

The present technology is directed to compounds, compositions, and methods related to non-morphinan-like kappa opioid receptor (KOR) antagonists. The technology is suited to treat addiction, diuresis, depression, post traumatic stress disorder, an eating disorder, panic disorder, social anxiety disorder, general anxiety disorder, obsessive compulsive disorders, excessive or unreasonable specific phobias, and/or other conditions related to anxiety or aversion-reward responses.

18 Claims, 3 Drawing Sheets

(56) References Cited

OTHER PUBLICATIONS

Raehal, K.M., Schmid, C.L., Medvedev, I.O., Gainetdinov, R.R., Premont, R.T., Bohn, L.M. Morphine-induced physiological and behavioral responses in mice lacking G protein-coupled receptor kinase 6. Drug and alcohol dependence. 2009, 104(3):187-96.

Ruchelman, A. L.; Houghton, P. J.; Zhou, N.; Liu, A.; Liu, L. F.; LaVoie, E. J. 5-(2-Aminoethyl)dibenzo[c,h][1,6]naphthyridin-6-ones: Variation of N-Alkyl Substituents Modulates Sensitivity to Efflux Transporters Associated with Multidrug Resistance. J Med. Chem. 2005, 48, 792-804.

Schmid, C. L.; Streicher, J.M.; Groer, C. E.; Munro, T. A.; Zhou, L.; Bohn, L. M. Functional Selectivity of 6'-Guanidinonaltrindole (6'-GNTI) at kappa-Opioid Receptors in Striatal Neurons. J Biol. Chem. 2013, 288, 22387-22398.

Tarselli M.A., et al. Synthesis of conolidine, a potent non-opiod analgesic for tonic and persistent pain. Nat. Chem. 2011, 3(6): 449-53.

Zhou, L.; Lovell, K. M.; Frankowski, K. J.; Slauson, S. R.; Phillips, A. M. Streicher, J. M.; Stahl, E.; Schmid, C. L.; Hodder, P.; Madoux, F.; Cameron, M. D.; Prisinzano, T. E.; Aube, J.; Bohn, L. M. Development of Functionally Selective, Small Molecule Agonists at Kappa Opioid Receptors. J Biol. Chem. 2013, 288, 36703-36716.

\* cited by examiner

AN4-015 Brain levels norBNI Brain levels

AN4-015 plasma levels norBNI plasma levels

ANTAGONISTS OF THE KAPPA OPIOID RECEPTOR

CROSS-REFERENCE TO RELATED APPLICATIONS

This application is a U.S. national phase application under 35 U.S.C. § 371 of International Application No. PCT/US2015/062708, filed on Nov. 25, 2015, which claims the benefit of and priority to U.S. Provisional Patent Application No. 62/084,932, filed Nov. 26, 2014, the entire disclosures of which are hereby incorporated by reference in their entireties for any and all purposes.

GOVERNMENT RIGHTS

This invention was made with government support under Grant Number R01-DA031927 awarded by the National Institutes of Health. The government has certain rights in the invention.

FIELD

The present technology is directed to compounds, compositions, and methods related to non-morphinan-like kappa opioid receptor (KOR) antagonists. The technology is suited to treat addiction, diuresis, depression, post-traumatic stress disorder, an eating disorder, panic disorder, social anxiety disorder, general anxiety disorder, obsessive compulsive disorders, excessive or unreasonable specific phobias, and/or other conditions related to anxiety or aversion-reward responses.

SUMMARY

In an aspect, a compound according to formula I is provided

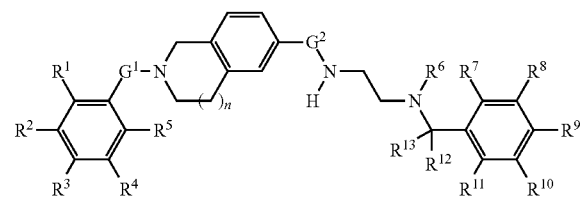

where $G^1$ and $G^2$ are each independently C=O or $S(O)_2$; $R^1$, $R^2$, $R^3$, $R^4$, $R^5$, $R^7$, $R^8$, $R^9$, $R^{10}$, and $R^{11}$ are each independently H, halo, hydroxy, amino, cyano, trifluoromethyl, thiol, alkylthio, sulfoxide, sulfone, nitro, pentafluorosulfanyl, carboxylate, amide, ester, or a substituted or unsubstituted $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, or aryloyloxy group, where any two adjacent $R^1$, $R^2$, $R^3$, $R^4$, $R^5$, $R^7$, $R^8$, $R^9$, $R^{10}$, and $R^{11}$ may join to form a 5-membered or 6-membered substituted or unsubstituted heteroalkyl group; $R^6$ is a branched $C_1$-$C_8$ alkyl group or a substituted or unsubstituted cycloalkyl or aryl group; $R^{12}$ and $R^{13}$ are each independently H or a substituted or unsubstituted $C_1$-$C_8$ alkyl or $C_5$-$C_7$ cycloalkyl group; and n is 0, 1, or 2; or stereoisomers, tautomers, solvates, and/or salts thereof; provided that when $G^1$ is $S(O)_2$, $G^2$ is C=O, $R^1$, $R^2$, $R^4$, $R^5$, $R^7$, $R^8$, $R^9$, $R^{10}$, $R^{11}$, $R^{12}$, $R^{13}$ are each H, $R^6$ is isopropyl, and n is 1, then $R^3$ is not methyl.

In a related aspect, a composition is provided that includes the compound of any one of the above embodiments and a pharmaceutically acceptable carrier.

In another aspect, a pharmaceutical composition is provided, the pharmaceutical composition including an effective amount of the compound of any one of the above embodiments for treating a condition, wherein the condition is addiction, diuresis, depression, post-traumatic stress disorder, an eating disorder, panic disorder, social anxiety disorder, general anxiety disorder, obsessive compulsive disorders, excessive or unreasonable specific phobias, and/or other conditions related to anxiety or aversion-reward responses.

In another aspect, a method is provided that includes administering an effective amount of a compound of any one of the above embodiments, or administering a pharmaceutical composition including an effective amount of a compound of any one of the above embodiments, to a subject suffering from addiction, diuresis, depression, post-traumatic stress disorder, an eating disorder, panic disorder, social anxiety disorder, general anxiety disorder, obsessive compulsive disorders, excessive or unreasonable specific phobias, and/or other conditions related to anxiety or aversion-reward responses.

In another aspect, a method is provided that includes inhibiting β-arrestin recruitment in a subject by administering an effective amount of a compound of any one of the above embodiments. The subject may be suffering from addiction, diuresis, depression, post-traumatic stress disorder, an eating disorder, panic disorder, social anxiety disorder, general anxiety disorder, obsessive compulsive disorders, excessive or unreasonable specific phobias, and/or other conditions related to anxiety or aversion-reward responses. In any embodiment herein, the subject may be suffering from addiction. The subject may be suffering from addiction to at least one of nicotine, ethanol, cocaine, opioids, amphetamines, marijuana, and synthetic cannabinoid agonists. The method may include inhibiting β-arrestin2 recruitment.

In another aspect, a method is provided for treating an addiction in a subject where the method includes administering an effective amount of a compound of any one of the above embodiments. In some embodiments, the addiction is to at least one of nicotine, ethanol, cocaine, opioids, amphetamines, marijuana, and synthetic cannabinoid agonists.

In an aspect, method of inhibiting β-arrestin recruitment is provided, where the method includes contacting a kappa opioid receptor with a compound of any one of the above embodiments. The method may include inhibiting β-arrestin2 recruitment.

DESCRIPTION OF THE DRAWINGS

FIGS. 1A and 1B show the concentration of a compound of the present technology and norBNI (respectively) in brain tissue, and FIGS. 1C and 1D show the concentration of a compound of the present technology and norBNI (respectively) in plasma.

DETAILED DESCRIPTION

Figure 1A:
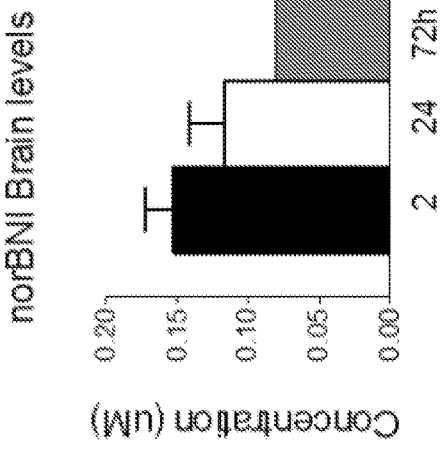
FIGS. 1A-D shows the results of experiments comparing the detected concentrations of a compound of the present technology with a morphinan-like opioid antagonist, norBNI, in the plasma and brain tissue of mice over the time period necessary for clearance (or up to 72 h) following a single 10 mg/kg IP dose.

In various aspects, the present technology provides compounds and methods for antagonizing a kappa opioid receptor. The compounds provided herein can be formulated into pharmaceutical compositions and medicaments that are useful in the disclosed methods. Also provided is the use of the compounds in preparing pharmaceutical formulations and medicaments.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{70}$ and —C(O)O-G groups. R$^{70}$ is a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$^{71}$R$^{72}$, and —NR$^{71}$C(O)R$^{72}$ groups, respectively. R$^{71}$ and R$^{72}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{71}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{73}$C(O)OR$^{74}$ and —OC(O)NR$^{73}$R$^{74}$ groups, respectively. R$^{73}$ and R$^{74}$ are independently a substituted or unsubstituted alkyl, alkenyl, alkynyl, cycloalkyl, aryl, aralkyl, heterocyclylalkyl, or heterocyclyl group as defined herein. R$^{73}$ may also be H.

The term "amine" (or "amino") as used herein refers to —NR$^{75}$R$^{76}$ groups, wherein R$^{75}$ and R$^{76}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{78}$R$^{79}$ and —NR$^{78}$SO$_2$R$^{79}$ groups, respectively. R$^{78}$ and R$^{79}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while "sulfides" include —SR$^{80}$ groups, "sulfoxides" include —S(O)R$^{81}$ groups, "sulfones" include —SO$_2$R$^{82}$ groups, and "sulfonyls" include —SO$_2$OR$^{83}$. R$^{80}$, R$^{81}$, R$^{82}$, and R$^{83}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{84}$—C(O)—NR$^{85}$R$^{86}$ groups. R$^{84}$, R$^{85}$, and R$^{86}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{87}$)NR$^{88}$R$^{89}$ and —NR$^{87}$C(NR$^{88}$)R$^{89}$, wherein R$^{87}$, R$^{88}$, and R$^{89}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{90}$C(NR$^{91}$)NR$^{92}$R$^{93}$, wherein R$^{90}$, R$^{91}$, R$^{92}$ and R$^{93}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{94}$)=C(R$^{95}$)NR$^{96}$R$^{97}$ and —NR$^{94}$C(R$^{95}$)=C(R$^{96}$)R$^{97}$, wherein R$^{94}$, R$^{95}$, R$^{96}$ and R$^{97}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O—. A "hydroxyalkyl" group is a hydroxyl-substituted alkyl group, such as HO—CH$_2$—.

The term "imide" refers to —C(O)NR$^{98}$C(O)R$^{99}$, wherein R$^{98}$ and R$^{99}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{100}$(NR$^{101}$) and —N(CR$^{100}$R$^{101}$) groups, wherein R$^{100}$ and R$^{101}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{100}$ and R$^{101}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkyl ammonium" refers to a —N(alkyl)$_3$ group. A trialkylammonium group is positively charged and thus typically has an associated anion, such as halogen anion.

The term "isocyano" refers to —NC.

The term "isothiocyano" refers to —NCS.

The term "pentafluorosulfanyl" refers to —SF$_5$.

The term "addictive substance" refers to those substances that when internalized can generate a compulsive desire and/or need for the addictive substance that is habit forming. Without being bound by theory, addictive substances activates the reward pathways of the brain of a subject in some manner, leading to a desire to repeat the internalization of the addictive substance. Exemplary addictive substances include, but are not limited to, nicotine, ethanol, cocaine, opioids, amphetamines, marijuana, and synthetic cannabinoid agonists.

The phrase "selectively inhibits" as used herein will be understood by persons of ordinary skill in the art and will vary to some extent depending upon the context in which the phrase is used. If there are uses of the phrase which are not clear to persons of ordinary skill in the art, given the context in which the phrase is used, the phrase at minimum refers to the compounds acting through a specific mechanism of action, resulting in fewer off-target effects because the compounds target a particular receptor over other receptors, such as a kappa opioid receptor over a g opioid receptor (MOR) and/or a δ opioid receptor (DOR), and or because the compounds target a particular mechanism such as β-arrestin recruitment and/or β-arrestin2 recruitment over other mechanisms. The phrase may further be modified as discussed herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

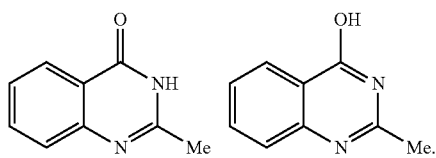

As another example, guanidines may exhibit the following isomeric forms in protic organic solution, also referred to as tautomers of each other:

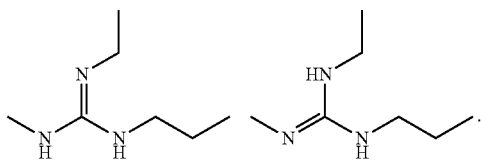

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Activation of the kappa opioid receptor (KOR) by endogenous neuropeptides, primarily dynorphin, initiates complex signaling cascades. The downstream effects of KOR agonism vary greatly and include antinociception, dysphoria and anxiety, though the details of the pharmacological pathways are still being elucidated. In contrast, KOR antagonists have been investigated as therapeutic treatments for addiction, diuresis, depression, post-traumatic stress disorder, an eating disorder, panic disorder, social anxiety disorder, general anxiety disorder, obsessive compulsive disorders, excessive or unreasonable specific phobias, as well as other conditions related to anxiety or aversion-reward responses. Many canonical KOR antagonists (Scheme 1) are derived from or bear a structural element of morphinan opioids, such as the widely-utilized tool compounds norBNI, 5'-GNTI and JDTic.

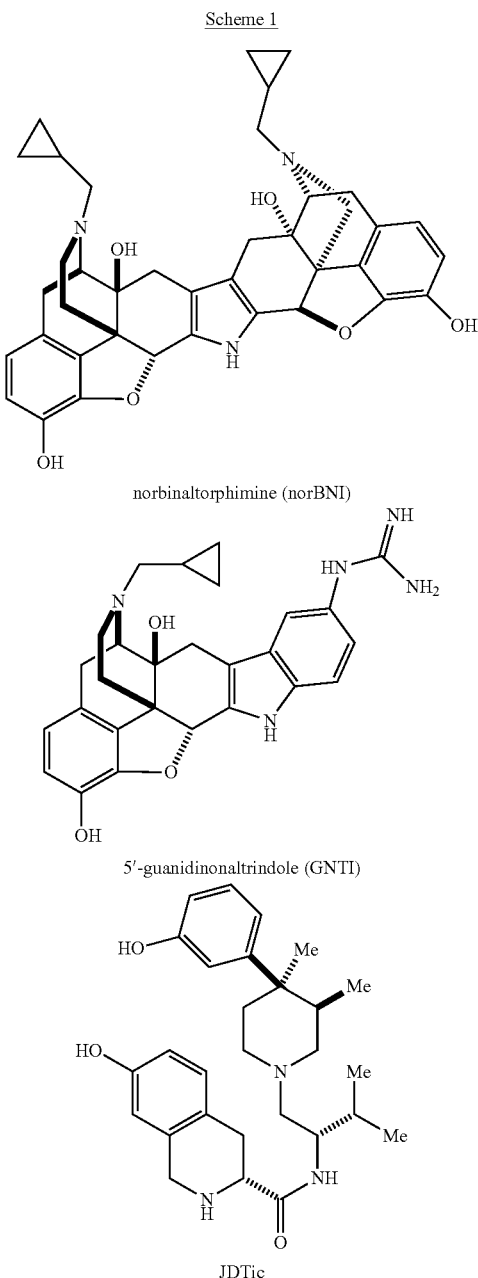

Scheme 1

Furthermore, many known KOR antagonists such as norBNI and JDTic are reported to have an extended duration of action, with effects of a single injection imparting antagonism in rodent models from a period of days up to months. There has been some controversy as to what causes these long term effects, whether it is due to adaptive signaling downstream of the antagonists ("adaptive plasticity"), or a depot effect wherein the compound is retained in tissues. For example, norBNI has been detected in brain tissue after more than 21 days (Patkar, K. A.; Wu, J.; Ganno, M. L.; Singh, H. D.; Ross, N. C.; Rasakham, K.; Toll, L.; McLaughlin, J. P. Physical presence of nor-binaltorphimine in mouse brain over 21 days after a single administration corresponds to its long-lasting antagonistic effect on kappa opioid receptors. *J. Pharmacol. Exp. Ther.* 2013, 346, 545-554.). However, irrespective of whether there is a depot effect, adaptive plasticity, or some other mechanism, such extended durations limit the therapeutic uses of such compounds in patients.

In contrast to the better-established chemotypes noted, the compounds of the present technology are highly modular, possesses no stereogenic centers, and bear little structural similarity to morphinan-like opioid ligands. Moreover, the compounds of the present technology have a clearance rate of less than about 12 h, a duration of action that allows for a more safe and effective therapeutic regime for KOR antagonists.

In an aspect, a compound according to formula I is provided

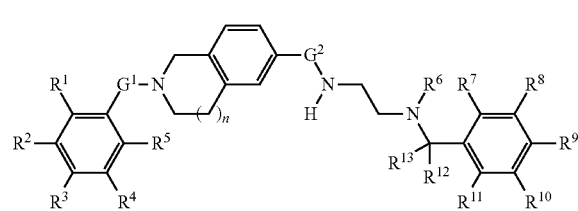

I or stereoisomers, tautomers, solvates, and/or salts thereof, where $G^1$ and $G^2$ are each independently C=O or S(O)$_2$; $R^1$, $R^2$, $R^3$, $R^4$, $R^5$, $R^7$, $R^8$, $R^9$, $R^{10}$, and $R^{11}$ are each independently H, halo, hydroxy, amino, cyano, trifluoromethyl, thiol, alkylthio, sulfoxide, sulfone, nitro, pentafluorosulfanyl, carboxylate, amide, ester, or a substituted or unsubstituted $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, or aryloyloxy group, where any two adjacent $R^1$, $R^2$, $R^3$, $R^4$, $R^5$, $R^7$, $R^8$, $R^9$, $R^{10}$, and $R^{11}$ may join to form a 5-membered or 6-membered substituted or unsubstituted heteroalkyl group; $R^6$ is a branched $C_1$-$C_8$ alkyl group or a substituted or unsubstituted cycloalkyl or aryl group; $R^{12}$ and $R^{13}$ are each independently H or a substituted or unsubstituted $C_1$-$C_8$ alkyl or $C_5$-$C_7$ cycloalkyl group; and n is 0, 1, or 2; provided that when $G^1$ is S(O)$_2$, $G^2$ is C=O, $R^1$, $R^2$, $R^4$, $R^5$, $R^7$, $R^8$, $R^9$, $R^{10}$, $R^{11}$, $R^{12}$, $R^{13}$ are each H, $R^6$ is isopropyl, and n is 1, then $R^3$ is not methyl.

In any embodiment herein, it may be at least one of $R^1$, $R^2$, $R^3$, $R^4$, $R^5$, $R^7$, $R^8$, $R^9$, $R^{10}$, or $R^{11}$ is halo, hydroxy, cyano, trifluoromethyl, thiol, alkylthio, nitro, pentafluorosulfanyl, carboxylate, ester, or a substituted or unsubstituted $C_1$-$C_6$ alkyl, $C_1$-$C_6$ alkoxy, aryl, aryloxy, $C_1$-$C_6$ alkanoyl, $C_1$-$C_6$ alkanoyloxy, aryloyl, or aryloyloxy group. In may be that at least one of $R^1$, $R^2$, $R^3$, $R^4$, $R^5$, $R^7$, $R^8$, $R^9$, $R^{10}$, or $R^{11}$ is halo, hydroxy, cyano, trifluoromethyl, thiol, alkylthio, sulfoxide, sulfone, pentafluorosulfanyl, carboxylate, ester, or a substituted or unsubstituted $C_1$-$C_6$ alkoxy, aryl, aryloxy, $C_1$-$C_6$ alkanoyl, $C_1$-$C_6$ alkanoyloxy, aryloyl, or aryloyloxy group. In any embodiment herein, it may be that at least one of $R^1$, $R^2$, $R^3$, $R^4$, $R^5$, $R^7$, $R^8$, $R^9$, $R^{10}$, or $R^{11}$ is halo, hydroxy, cyano, alkylthio, sulfone, carboxylate, ester, or a substituted or unsubstituted $C_1$-$C_6$ alkoxy, aryloxy, $C_1$-$C_6$ alkanoyl, $C_1$-$C_6$ alkanoyloxy, aryloyl, or aryloyloxy group. In any embodiment herein, it may be that at least one of $R^1$, $R^2$, $R^3$, $R^4$, $R^5$, $R^7$, $R^8$, $R^9$, $R^{10}$, or $R^{11}$ is halo, hydroxy, carboxylate, ester, or a substituted or unsubstituted $C_1$-$C_6$ alkoxy, $C_1$-$C_6$ alkanoyl, or $C_1$-$C_6$ alkanoyloxy group. In any embodiment herein, it may be that at least one of $R^1$, $R^2$, $R^3$, $R^4$, $R^5$, $R^7$, $R^8$, $R^9$, $R^{10}$, or $R^{11}$ is hydroxy or a substituted or unsubstituted $C_1$-$C_6$ alkoxy or $C_1$-$C_6$ alkanoyloxy group. In any embodiment herein, it may be that at least one of $R^1$, $R^2$, $R^3$, $R^4$, $R^5$, $R^7$, $R^8$, $R^9$, $R^{10}$, or $R^{11}$ is hydroxy or an unsubstituted $C_1$-$C_6$ alkoxy group.

At least one of $R^1$, $R^2$, $R^3$, $R^4$, or $R^5$ may be halo, hydroxy, carboxylate, ester, or a substituted or unsubstituted $C_1$-$C_6$ alkyl, $C_1$-$C_6$ alkoxy, $C_1$-$C_6$ alkanoyl, or $C_1$-$C_6$ alkanoyloxy group. In any embodiment herein, at least one of $R^7$, $R^8$, $R^9$, $R^{10}$, or $R^{11}$ may be halo, hydroxy, cyano, trifluoromethyl, thiol, alkylthio, sulfoxide, sulfone, nitro, pentafluorosulfanyl, carboxylate, ester, or a substituted or unsubstituted $C_1$-$C_6$ alkyl, $C_1$-$C_6$ alkoxy, aryl, aryloxy, $C_1$-$C_6$ alkanoyl, $C_1$-$C_6$ alkanoyloxy, aryloyl, or aryloyloxy group. In any embodiment herein, it may be that at least one of $R^7$, $R^8$, $R^9$, $R^{10}$, or $R^{11}$ is halo, hydroxy, trifluoromethyl, carboxylate, ester, or a substituted or unsubstituted $C_1$-$C_6$ alkyl, $C_1$-$C_6$ alkoxy, $C_1$-$C_6$ alkanoyl, or $C_1$-$C_6$ alkanoyloxy group. In any embodiment herein, it may be that at least one of $R^7$, $R^8$, $R^9$, $R^{10}$, or $R^{11}$ is hydroxy or an unsubstituted $C_1$-$C_6$ alkoxy group.

At least two of $R^1$, $R^2$, $R^3$, $R^4$, $R^5$, $R^7$, $R^8$, $R^9$, $R^{10}$, or $R^{11}$ may each independently be halo, hydroxy, cyano, trifluoromethyl, nitro, pentafluorosulfanyl, carboxylate, ester, or a substituted or unsubstituted $C_1$-$C_6$ alkyl, $C_1$-$C_6$ alkoxy, aryl, aryloxy, $C_1$-$C_6$ alkanoyl, $C_1$-$C_6$ alkanoyloxy, aryloyl, or aryloyloxy group. It may be that at least two of $R^1$, $R^2$, $R^3$, $R^4$, $R^5$, $R^7$, $R^8$, $R^9$, $R^{10}$, or $R^{11}$ are each independently halo, hydroxy, carboxylate, ester, or a substituted or unsubstituted $C_1$-$C_6$ alkyl, $C_1$-$C_6$ alkoxy, $C_1$-$C_6$ alkanoyl, or $C_1$-$C_6$ alkanoyloxy group. In any embodiment herein, it may be that at least two of $R^1$, $R^2$, $R^3$, $R^4$, $R^5$, $R^7$, $R^8$, $R^9$, $R^{10}$, or $R^{11}$ are each independently halo, hydroxy, or a substituted or unsubstituted $C_1$-$C_6$ alkyl or $C_1$-$C_6$ alkoxy group.

In any of the above embodiments, it may be that one of $R^1$, $R^2$, $R^3$, $R^4$ or $R^5$ is halo, hydroxy, amino, cyano, trifluoromethyl, nitro, pentafluorosulfanyl, carboxylate, amide, ester, or a substituted or unsubstituted $C_1$-$C_6$ alkyl, $C_1$-$C_6$ alkoxy, aryl, aryloxy, $C_1$-$C_6$ alkanoyl, $C_1$-$C_6$ alkanoyloxy, aryloyl, or aryloyloxy group; and the remaining $R^1$, $R^2$, $R^3$, $R^4$, or $R^5$ are each H. In any of the above embodiments, it may be that any two adjacent $R^1$, $R^2$, $R^3$, $R^4$, $R^5$, $R^7$, $R^8$, $R^9$, $R^{10}$, and $R^{11}$ may join to form a dioxolanyl or dioxanyl group. In any of the above embodiments, it may be that n is 1. In any of the above embodiments, it may be that $G^1$ is S(O)$_2$. In any of the above embodiments, it may be that $G^2$ is C=O. In any of the above embodiments, it may be that $R^6$ is a branched $C_1$-$C_8$ alkyl group or a substituted or unsubstituted cycloalkyl group. In any of the above embodiments, it may be that $R^6$ is isopropyl, sec-butyl, tert-butyl, isopentyl, neopentyl, or adamantyl. In any of the above embodiments, it may be that $R^6$ is tert-butyl, neopentyl, or adamantyl.

In any of the above embodiments, it may be that when $G^1$ is S(O)$_2$, $G^2$ is C=O, $R^1$, $R^2$, $R^4$, $R^5$, $R^7$, $R^8$, $R^9$, $R^{10}$, $R^{11}$, $R^{12}$, $R^{13}$ are each H, and $R^6$ is isopropyl, then $R^3$ is not an unsubstituted linear alkyl group. In any of the above embodiments, it may be that when $G^1$ is S(O)$_2$, $G^2$ is C=O, $R^1$, $R^2$, $R^4$, $R^5$, $R^7$, $R^8$, $R^9$, $R^{10}$, $R^{11}$, $R^{12}$, $R^{13}$ are each H, and $R^6$ is isopropyl, then $R^3$ is not an unsubstituted alkyl group. In any of the above embodiments, it may be that when $G^1$ is $S(O)_2$, $G^2$ is C=O, $R^1$, $R^2$, $R^4$, $R^5$, $R^7$, $R^8$, $R^9$, $R^{10}$, $R^{11}$, $R^{12}$, $R^{13}$ are each H, and $R^6$ is isopropyl, then $R^3$ is not an alkyl group.

In any embodiment herein, it may be that $G^1$ is $S(O)_2$; $G^2$ is C=O; $R^1$, $R^4$, $R^5$, $R^7$, $R^{10}$, and $R^{11}$ are each H; $R^2$, $R^3$, $R^8$, and $R^9$ are each independently halo, hydroxy, amino, cyano, trifluoromethyl, thiol, alkylthio, sulfoxide, sulfone, nitro, pentafluorosulfanyl, carboxylate, amide, ester, or a substituted or unsubstituted $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, or aryloyloxy group, where any two adjacent $R^2$, $R^3$, $R^8$, and $R^9$ may join to form a 5-membered or 6-membered substituted or unsubstituted heteroalkyl group; $R^6$ is a branched $C_1$-$C_8$ alkyl group; $R^{12}$ and $R^{13}$ are each H; and n is 1.

In any embodiment herein, it may be that $G^1$ is $S(O)_2$; $G^2$ is C=O; $R^1$, $R^4$, $R^5$, $R^7$, $R^{10}$, and $R^{11}$ are each H; one of $R^2$ and $R^3$ is halo, hydroxy, or a unsubstituted $C_1$-$C_6$ alkyl, $C_1$-$C_6$ alkoxy, $C_1$-$C_6$ alkanoyl, or $C_1$-$C_8$ alkanoyloxy group and the other $R^2$ or $R^3$ is H; one of $R^8$ and $R^9$ is halo, hydroxy, amino, cyano, trifluoromethyl, thiol, alkylthio, sulfoxide, sulfone, nitro, pentafluorosulfanyl, carboxylate, amide, ester, or a substituted or unsubstituted $C_1$-$C_6$ alkoxy, $C_1$-$C_6$ alkanoyl, or $C_1$-$C_8$ alkanoyloxy group, and the other $R^8$ or $R^9$ is H; $R^6$ is a branched $C_1$-$C_8$ alkyl group; $R^{12}$ and $R^{13}$ are each H; and n is 1.

In any of the above embodiments, it may be that the compound is selected from

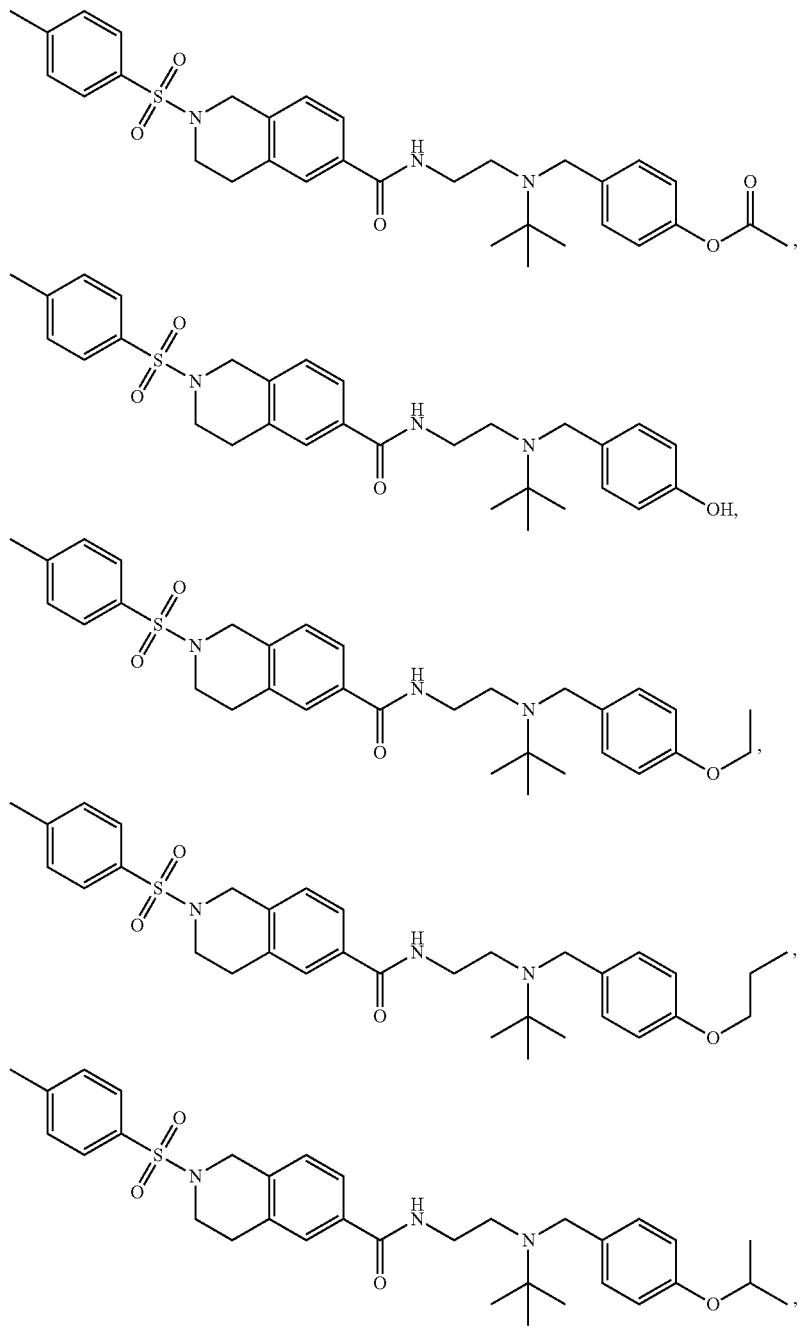

-continued
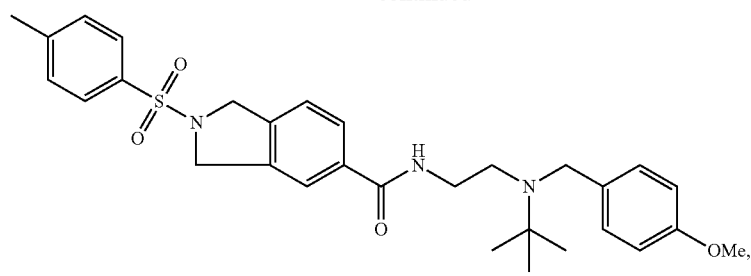
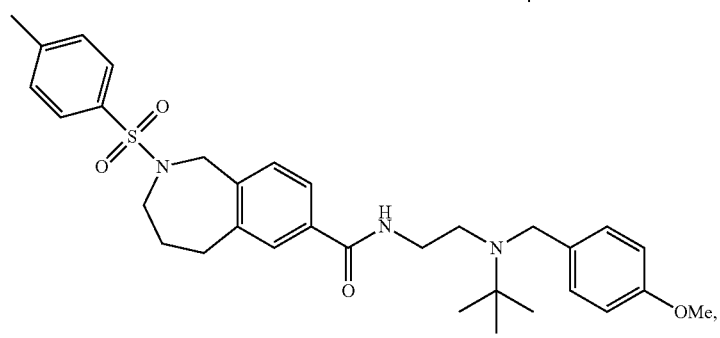
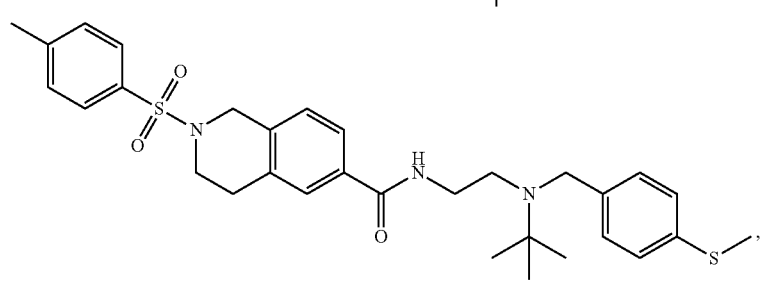
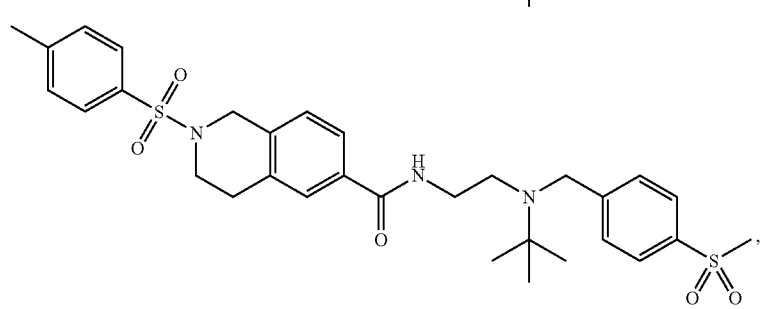
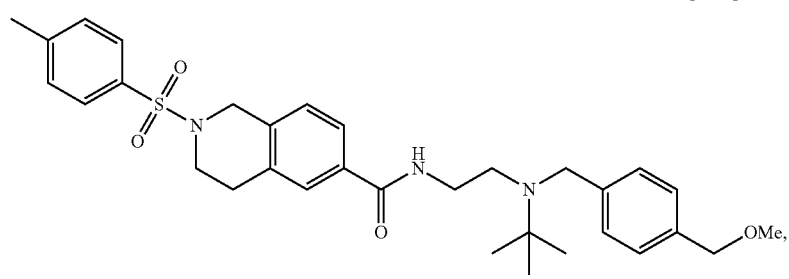
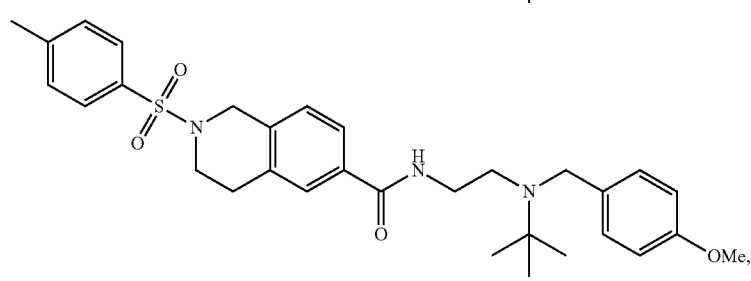

-continued
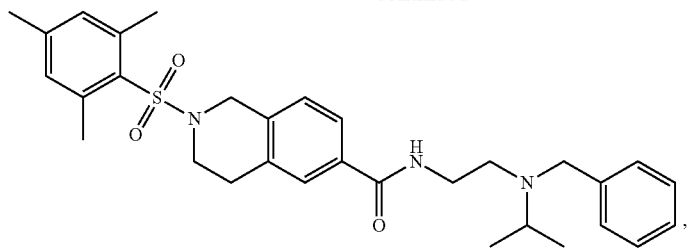
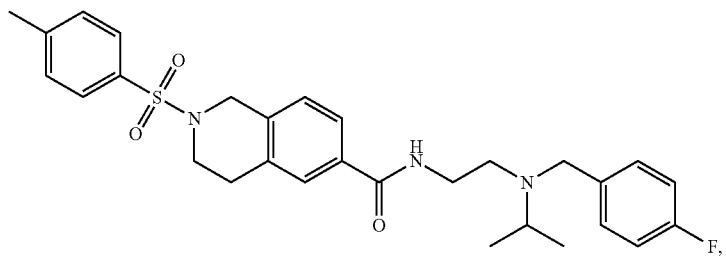
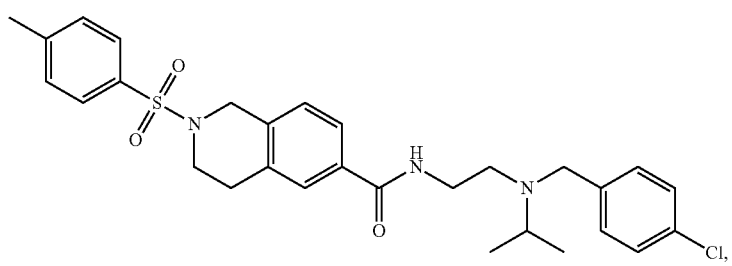
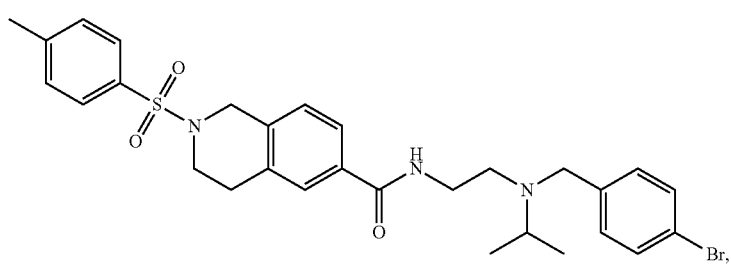
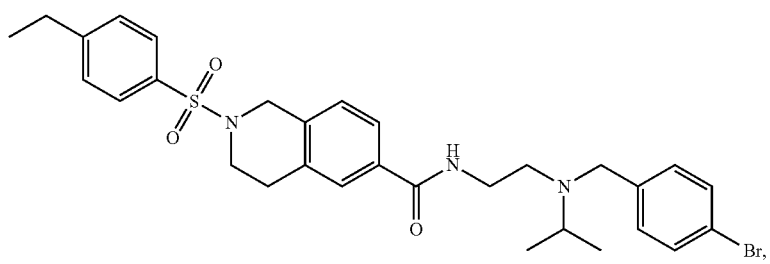
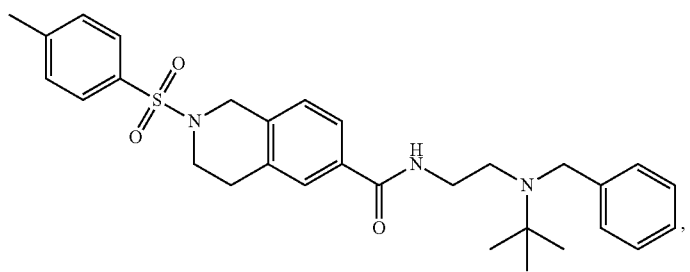

-continued
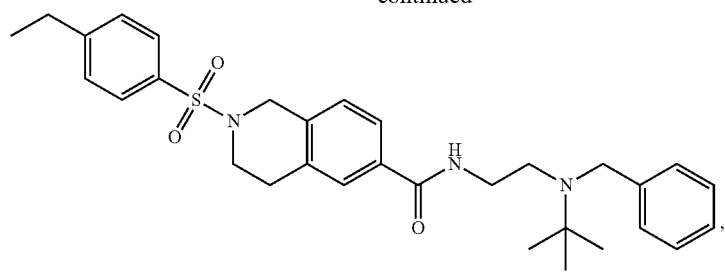
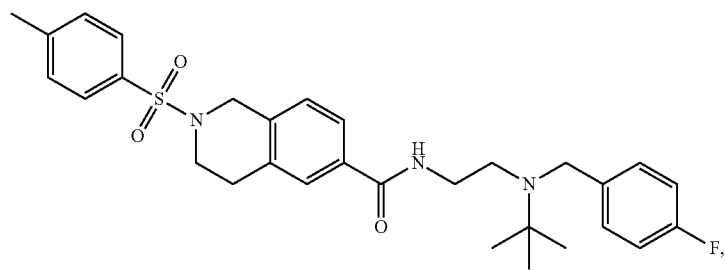
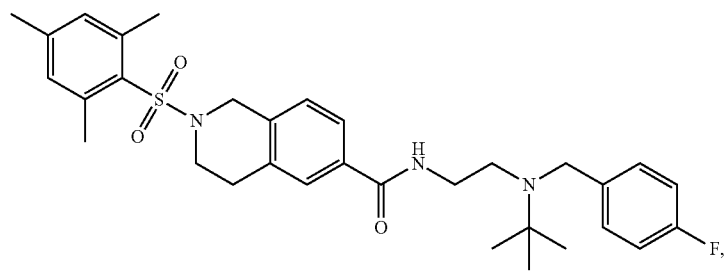
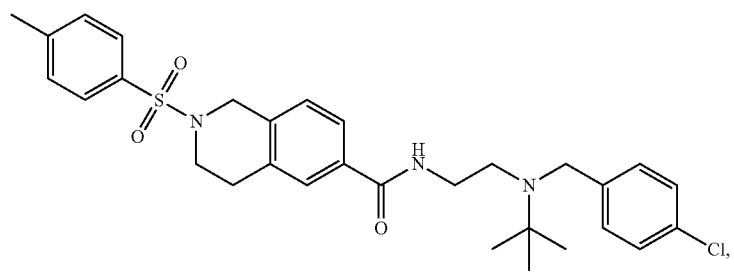
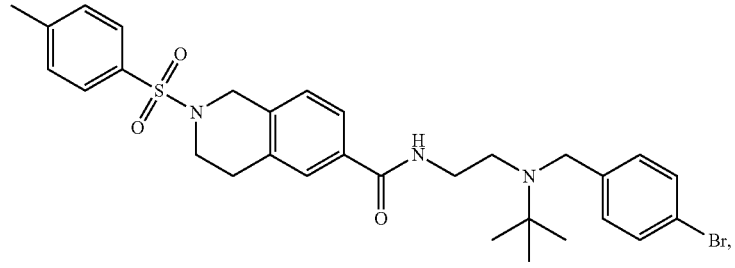
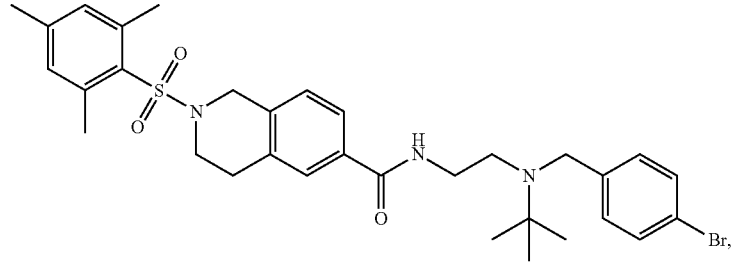

-continued
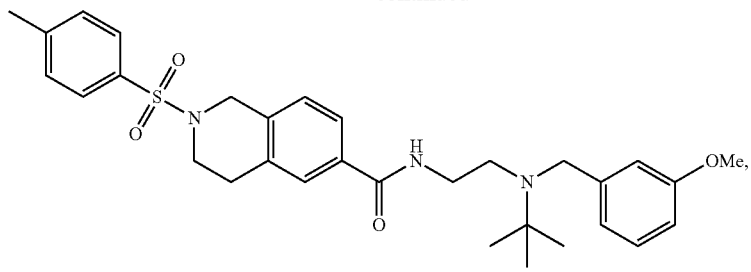
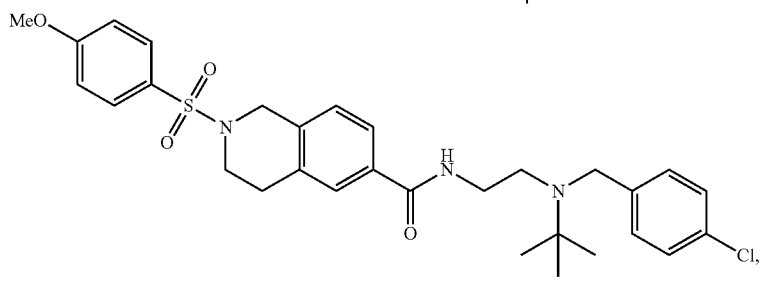
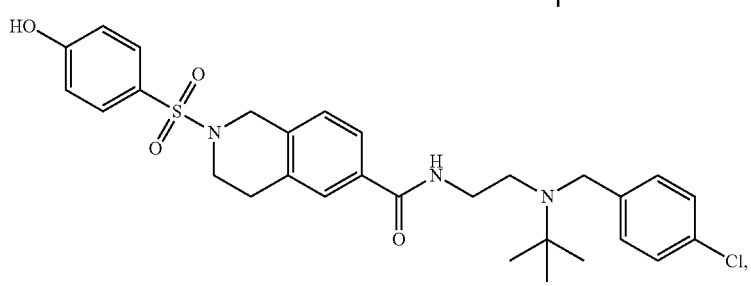
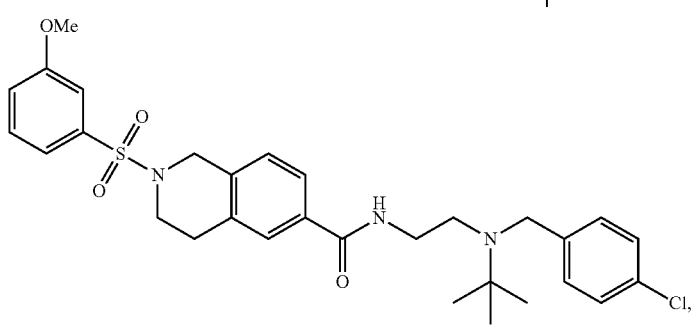
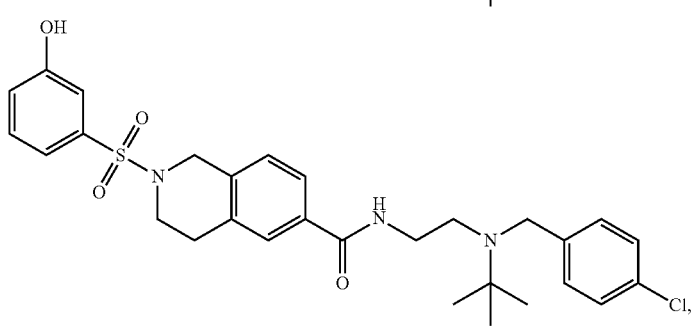
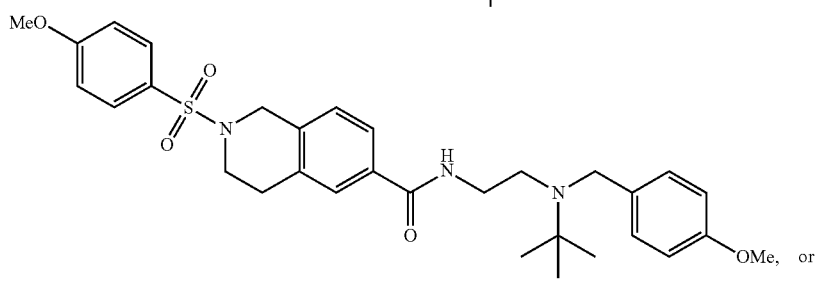

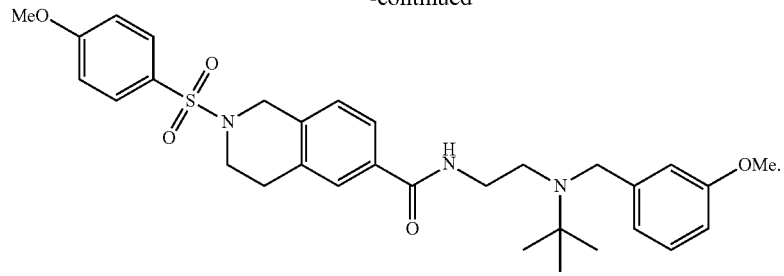
In any of the above embodiments, it may be that the compound is selected from
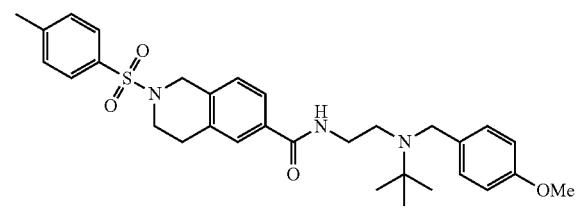
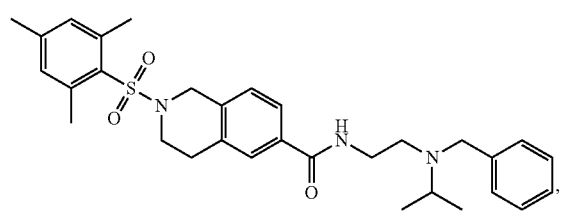
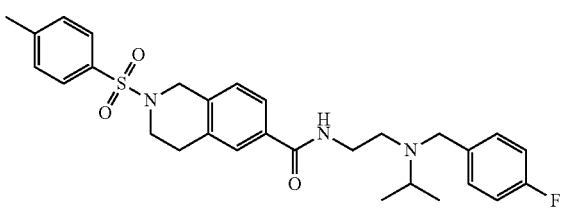
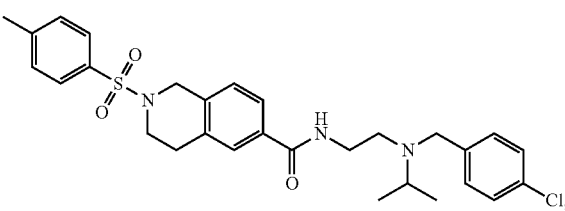
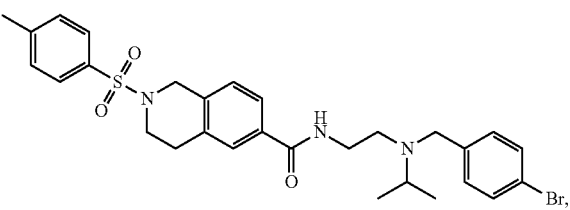
-continued
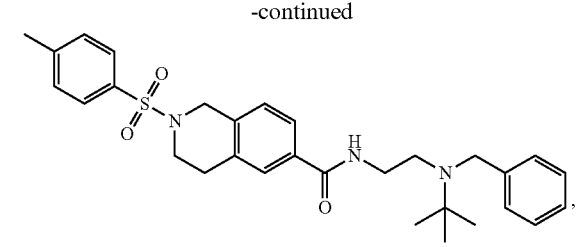
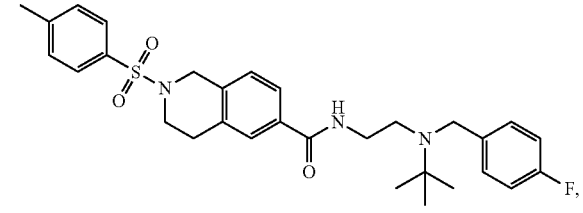
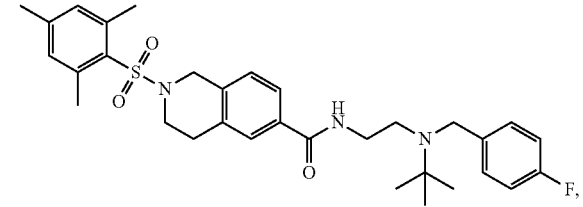
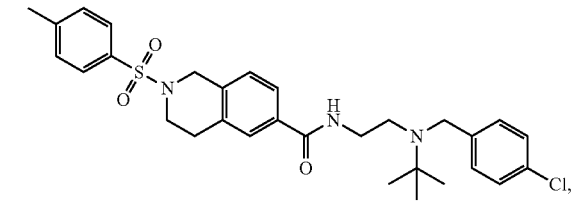
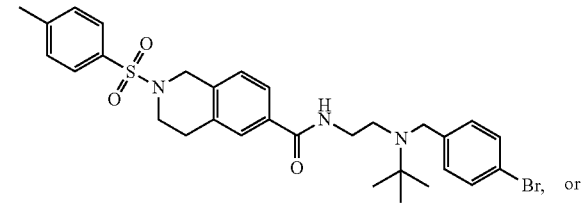

-continued

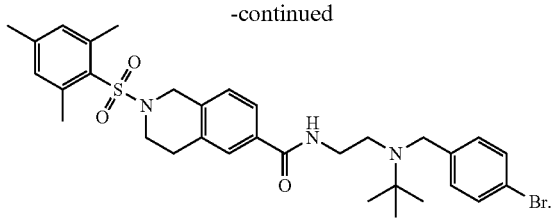

In an aspect of the present technology, a composition is provided that includes any one of the aspects and embodiments of compounds of formula I and a pharmaceutically acceptable carrier. In a related aspect, a pharmaceutical composition is provided, the pharmaceutical composition including an effective amount of the compound of any one of the aspects and embodiments of compounds of formula I for treating a condition; and where the condition is addiction, diuresis, depression, post-traumatic stress disorder, an eating disorder, panic disorder, social anxiety disorder, general anxiety disorder, obsessive compulsive disorders, excessive or unreasonable specific phobias, and/or other conditions related to anxiety or aversion-reward responses. In a further related aspect, a method is provided that includes administering an effective amount of a compound of any one of the aspects and embodiments of compounds of formula I or administering a pharmaceutical composition comprising an effective amount of a compound of any one of the aspects and embodiments of compounds of formulas I to a subject suffering from addiction, diuresis, depression, post traumatic stress disorder, an eating disorder, panic disorder, social anxiety disorder, general anxiety disorder, obsessive compulsive disorders, excessive or unreasonable specific phobias, and/or other conditions related to anxiety or aversion-reward responses.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of alcohol addiction. Another example of an effective amount includes amounts or dosages that are capable of reducing symptoms associated with metabolic syndrome, such as, for example, obesity and/or cardiometabolic abnormalities. The effective amount of the compound may selectively antagonize the kappa opioid receptor (KOR). The effective amount of the compound may selectively bind to the KOR at least about 5 times more than the δ opioid receptor (DOR); thus, the effective amount of the compound may selectively bind to the KOR at least about 10 times, at least about 25 times, at least about 50 times, or at least about 100 times more than the DOR. In any embodiment herein, including any of the above embodiments regarding the DOR, the effective amount of the compound may selectively bind to the KOR at least about 5 times more than the μ opioid receptor (MOR); thus, it may be that the effective amount of the compound selectively binds to the KOR at least about 10 times more, at least 25 times more, at least about 50 times more, or at least about 100 times more than the MOR. As used herein, a "subject" or "patient" is a mammal, such as a cat, dog, rodent or primate. Typically the subject is a human, and, preferably, a human suffering from or suspected of suffering from an addiction. The term "subject" and "patient" can be used interchangeably.

Thus, the instant present technology provides pharmaceutical compositions and medicaments comprising any of the compounds disclosed herein (e.g., compounds of formulas I) and a pharmaceutically acceptable carrier or one or more excipients or fillers. The compositions may be used in the methods and treatments described herein. Such compositions and medicaments include a therapeutically effective amount of any compound as described herein, including but not limited to a compound of formula I. The pharmaceutical composition may be packaged in unit dosage form. The unit dosage form is effective in treating addiction by reducing desire for an addictive substance(s), and/or effective in treating a metabolic disorder by reducing symptoms associated with the metabolic disorder when administered to a subject in need thereof.

The pharmaceutical compositions and medicaments may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like to prevent and treat disorders associated with the effects of increased plasma and/or hepatic lipid levels. The compounds and compositions described herein may be used to prepare formulations and medicaments that prevent or treat a variety of disorders associated with addiction, diuresis, depression, post-traumatic stress disorder, an eating disorder, panic disorder, social anxiety disorder, general anxiety disorder, obsessive compulsive disorders, excessive or unreasonable specific phobias, and/or other conditions related to anxiety or aversion-reward responses. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until (for addiction) the motivation to internalize the addictive substance and/or relapse-like behavior is decreased or stopped, or (for metabolic syndrome and/or obesity) the elevated plasma or elevated white blood cell count or hepatic cholesterol or triglycerides or progression of the disease state is decreased or stopped. For metabolic syndrome and/or obesity, the progression of the disease state can be assessed using in vivo imaging, as described, or by taking a tissue sample from a patient and observing the target of interest therein. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

Effectiveness of the compositions and methods of the present technology may also be demonstrated by a decrease in the symptoms of an addiction, such as, for example, motivation to internalize the addictive substance and/or relapse-like behavior. Effectiveness of the compositions and methods of the present technology may also be demonstrated by a decrease in the symptoms of addiction, diuresis, depression, post-traumatic stress disorder, an eating disorder, panic disorder, social anxiety disorder, general anxiety disorder, obsessive compulsive disorders, excessive or unreasonable specific phobias, and/or other conditions related to anxiety or aversion-reward responses.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

In an aspect, a method is provided where the method includes inhibiting β-arrestin recruitment in a subject by administering an effective amount of a compound of any one of the aspects and embodiments of compounds of formula I. The subject may be suffering from addiction, diuresis, depression, post-traumatic stress disorder, an eating disorder, panic disorder, social anxiety disorder, general anxiety disorder, obsessive compulsive disorders, excessive or unreasonable specific phobias, and/or other conditions related to anxiety or aversion-reward responses. In any of the above embodiments, the addiction may be to at least one of nicotine, ethanol, cocaine, opioids, amphetamines, marijuana, or a synthetic cannabinoid agonist. In any embodiment herein, the method may include inhibiting β-arrestin2 recruitment.

In an aspect, a method for treating an addiction in a subject is provided that includes administering an effective amount of a compound of any one of the aspects and embodiments of compounds of formula I. The addiction may be to at least one of nicotine, ethanol, cocaine, opioids, amphetamines, marijuana, or a synthetic cannabinoid agonist. Administering the effective amount of the compound may include administering a pharmaceutical composition according to any embodiment described herein.

In an aspect, a method of inhibiting β-arrestin recruitment is provided that includes contacting a KOR with a compound of any one of the aspects and embodiments of compounds of formulas I. It may be the method includes contacting a KOR with an effective amount of a compound of any one of the aspects and embodiments of compounds of formulas I. Such methods may be performed outside of a subject, such as in an assay. A cell may include the KOR.

The compounds of the present technology can also be administered to a patient along with other conventional therapeutic agents that may be useful in the treatment of addiction, diuresis, depression, post-traumatic stress disorder, an eating disorder, panic disorder, social anxiety disorder, general anxiety disorder, obsessive compulsive disorders, excessive or unreasonable specific phobias, and/or other conditions related to anxiety or aversion-reward responses. The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent in an amount that can potentially or synergistically be effective for the treatment of addiction, diuresis, depression, post traumatic stress disorder, an eating disorder, panic disorder, social anxiety disorder, general anxiety disorder, obsessive compulsive disorders, excessive or unreasonable specific phobias, and/or other conditions related to anxiety or aversion-reward responses.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1 \times 10^{-4}$ g/kg to 1 g/kg, preferably, $1 \times 10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

In another aspect, the present technology provides methods of identifying a target of interest including contacting the target of interest with a detectable or imaging effective quantity of a labeled compound of the present technology. A detectable or imaging effective quantity is a quantity of a labeled compound of the present technology necessary to be detected by the detection method chosen. For example, a detectable quantity can be an administered amount sufficient to enable detection of binding of the labeled compound to a target of interest including, but not limited to, a KOR. Suitable labels are known by those skilled in the art and can include, for example, radioisotopes, radionuclides, isotopes, fluorescent groups, biotin (in conjunction with streptavidin complexation), and chemiluminescent groups. Upon binding of the labeled compound to the target of interest, the target may be isolated, purified and further characterized such as by determining the amino acid sequence.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

General synthetic and analytical details:

All reagents and materials were purchased from commercial vendors (Sigma, Alfa Aesar, Oakwood or ASW Medchem) and used as received. Ethyl ether, toluene, THF, MeCN and $CH_2Cl_2$ were degassed with nitrogen and passed through two columns of basic alumina on an Innovative Technology solvent purification system. $^1H$ and $^{13}C$ NMR spectra were recorded on a Bruker AM 400 spectrometer (operating at 400 and 100 MHz respectively) in $CDCl_3$ with 0.03% TMS as an internal standard, unless otherwise specified. Chemical shifts are reported in parts per million (ppm) downfield from TMS. $^{13}C$ multiplicities were determined with the aid of an APT pulse sequence, differentiating the signals for methyl and methane carbons as "d" from methylene and quarternary carbons as "u". The infrared (IR) spectra were acquired as thin films using a universal ATR sampling accessory on a PerkinElmer Spectrum 100 FT-IR spectrometer and the absorption frequencies are reported in $cm^{-1}$. Melting points were determined on a Stanford Research Systems Optimelt automated melting point system interfaced through a PC and are uncorrected.

HPLC/MS analysis was carried out with gradient elution (5% $CH_3CN$ to 100% $CH_3CN$) on an Agilent 1200 RRLC with a photodiode array UV detector and an Agilent 6224 TOF mass spectrometer (also used to produce high resolution mass spectra). HPLC purification was carried out by mass directed fractionation (MDF) with gradient elution (a narrow $CH_3CN$ gradient was chosen based on the retention time of the target from LCMS analysis of the crude sample) on an Agilent 1200 instrument with photodiode array detector, an Agilent 6120 quadrupole mass spectrometer, and a HTPAL LEAP autosampler. Fractions were triggered using an MS and UV threshold determined by HPLC/MS analysis of the crude sample. One of two column/mobile phase conditions were chosen for both analysis and purification to promote the targets neutral state (0.02% formic acid with Waters Atlantis T3 5 um, 19×150 mm; or pH 9.8 $NH_4OH$ with Waters XBridge C18 5 um, 19×150 mm).

Representative General Synthetic Scheme

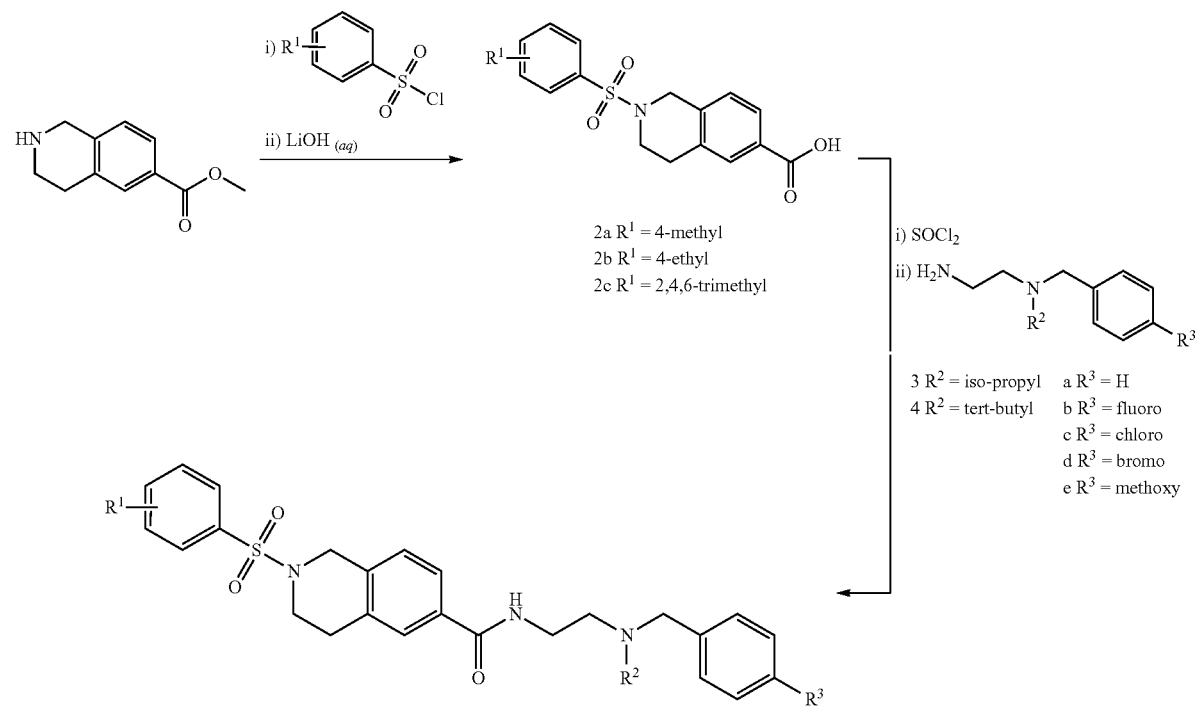

Synthesis of Carboxylic Acid Fragments 2a-2c

Example 1: Methyl 2-tosyl-1,2,3,4-tetrahydroisoquinoline-6-carboxylate

To a solution of methyl 1,2,3,4-tetrahydroisoquinoline-6-carboxylate (171 mg, 0.894 mmol) and triethylamine (271 mg, 2.68 mmol, 3.0 equiv) in $CH_2Cl_2$ (15 mL) was added p-toluenesulfonyl chloride (256 mg, 1.34 mmol, 1.5 equiv). The reaction was stirred at rt for 15 h, diluted with 1 N HCl and extracted with $CH_2Cl_2$. The combined organics were dried ($Na_2SO_4$), concentrated and purified by silica gel chromatography to afford the sulfonamide product as a white solid (231 mg, 0.669 mmol, 75% yield). Mp=143-145° C.; $R_f$=0.34 (25% EtOAc/hexanes); $^1$H NMR (400 MHz, $CDCl_3$) δ 2.41 (s, 3H), 2.96 (t, J=6.0 Hz, 2H), 3.36 (t, J=6.0 Hz, 2H), 3.88 (s, 3H), 4.28 (s, 2H), 7.10 (d, J=8.0 Hz, 1H), 7.33 (d, J=8.0 Hz, 2H), 7.72 (d, J=8.0 Hz, 2H), 7.77 (s, 1H), 7.79 (d, J=8.0 Hz, 1H); $^{13}$C NMR (101 MHz, $CDCl_3$, APT pulse sequence) δ d 21.5, 52.1, 126.6, 127.4, 127.7, 129.8, 130.2; u 28.8, 43.6, 47.7, 128.7, 133.2, 133.4, 136.9, 143.9, 166.7; IR 1718 $cm^{-1}$; HRMS (ESI) m/z calcd for $C_{18}H_{20}NO_4S$ ($[M+H]^+$) 346.1108, found 346.1116.

Example 2: 2-Tosyl-1,2,3,4-tetrahydroisoquinoline-6-carboxylic Acid (2a)

To a solution of the above methyl ester (298 mg, 0.765 mmol) in THF:MeOH:water (3:1:1, 10 mL) was added lithium hydroxide monohydrate (160 mg, 3.83 mmol, 5 equiv) and the reaction stirred at rt for 15 h. The THF and MeOH were removed in vacuo and the reaction concentrate was acidified with 2 N HCl, precipitating the carboxylic acid product as a sparingly soluble white solid (213 mg, 0.643 mmol, 84% yield), which was filtered, washed with water, dried under vacuum and used without further purification. Mp=234-240° C.; $R_f$=0.58 (10% MeOH and 2% AcOH in $CH_2Cl_2$); $^1$H NMR (400 MHz, DMSO-d6) δ 2.39 (s, 3H), 2.91 (t, J=6.0 Hz, 2H), 3.30 (t, J=6.0 Hz, 2H), 4.25 (s, 2H), 7.28 (d, J=8.0 Hz, 1H), 7.44 (d, J=8.0 Hz, 2H), 7.70-7.74 (complex, 4H), 12.89 (br s, 1H); $^{13}$C NMR (101 MHz, DMSO-d6, APT pulse sequence) δ d 21.0, 126.7, 126.9, 127.4, 129.7, 129.9; u 27.9, 43.3, 47.3, 129.1, 133.0, 133.4, 136.7, 143.7, 167.0; IR 1678 $cm^{-1}$; HRMS (ESI) m/z calcd for $C_{17}H_{16}NO_4S$ ($[M-H]^-$) 330.0806, found 330.0807.

Example 3: Methyl 2-((4-ethylphenyl)sulfonyl)-1,2,3,4-tetrahydroisoquinoline-6-carboxylate Methyl 1,2,3,4-tetrahydroisoquinoline-6-carboxylate (182 mg, 0.952 mmol) and 4-ethyl-benzenesulfonyl chloride (292 mg, 1.43 mmol, 1.5 equiv) were reacted according the protocol in Example 1 to afford the sulfonamide product as a white solid (285 mg, 0.793 mmol, 83% yield). Mp=128-130° C.; $R_f$=0.40 (25% EtOAc/hexanes); $^1$H NMR (400 MHz, $CDCl_3$) δ 1.23 (t, J=7.6 Hz, 3H), 2.69 (q, J=7.6 Hz, 2H), 2.95 (t, J=6.0 Hz, 2H), 3.36 (t, J=6.0 Hz, 2H), 3.87 (s, 3H), 4.28 (s, 2H), 7.09 (d, J=8.4 Hz, 1H), 7.35 (d, J=8.4 Hz, 2H), 7.74-7.79 (complex, 4H); $^{13}$C NMR (101 MHz, $CDCl_3$, APT pulse sequence) δ d 14.9, 51.9, 126.4, 127.2, 127.7, 128.5, 130.0; u 28.62, 28.65, 43.5, 47.6, 128.6, 133.2, 133.3, 136.8, 149.8, 166.5; IR 1717 $cm^{-1}$; HRMS (ESI) m/z calcd for $C_{19}H_{22}NO_4S$ ($[M+H]^+$) 360.1264, found 360.1274.

Example 4: 2-((4-Ethylphenyl)sulfonyl)-1,2,3,4-tetrahydroisoquinoline-6-carboxylic Acid (2b)

The above methyl ester (252 mg, 0.701 mmol) were reacted according the protocol in Example 2 to afford the carboxylic acid product as a sparingly soluble white solid (216 mg, 0.625 mmol, 89% yield), which was filtered, washed with water, dried under vacuum and used without further purification. Mp=208-213° C.; $R_f$=0.58 (10% MeOH and 2% AcOH in $CH_2Cl_2$); $^1$H NMR (400 MHz, DMSO-d6) δ 1.18 (t, J=7.6 Hz, 3H), 2.68 (q, J=7.6 Hz, 2H), 2.91 (t, J=6.0 Hz, 2H), 3.31 (t, J=6.0 Hz, 2H), 4.26 (s, 2H), 7.28 (d, J=8.0 Hz, 1H), 7.46 (d, J=8.0 Hz, 2H), 7.69-7.76 (complex, 4H), 12.91 (br s, 1H); $^{13}$C NMR (101 MHz, DMSO-d6, APT pulse sequence) δ d 15.0, 126.7, 126.8, 127.5, 128.7, 129.7; u 28.0, 43.3, 47.3, 129.1, 133.2, 133.4, 136.6, 149.6, 167.0; IR 1683 $cm^{-1}$; HRMS (ESI) m/z calcd for $C_{18}H_{20}NO_4S$ ($[M+H]^+$) 346.1113, found 346.1114.

Example 5: Methyl 2-((2,4,6-trimethylphenyl)sulfonyl)-1,2,3,4-tetrahydroisoquinoline-6-carboxylate Methyl 1,2,3,4-tetrahydroisoquinoline-6-carboxylate (191 mg, 0.999 mmol) and 2,4,6-trimethyl-benzenesulfonyl chloride (328 mg, 1.50 mmol, 1.5 equiv) were reacted according the protocol in Example 1 to afford the sulfonamide product as a white solid (188 mg, 0.503 mmol, 50% yield). Mp=142-143° C.; $R_f$=0.50 (25% EtOAc/hexanes); $^1$H NMR (400 MHz, $CDCl_3$) δ 2.29 (s, 3H), 2.63 (s, 6H), 2.91 (t, J=6.0 Hz, 2H), 3.47 (t, J=6.0 Hz, 2H), 3.89 (s, 3H), 4.40 (s, 2H), 6.96 (s, 2H), 7.12 (d, J=8.0 Hz, 1H), 7.81 (m, 2H); $^{13}$C NMR (101 MHz, $CDCl_3$, APT pulse sequence) δ d 21.0, 22.8, 52.1, 126.6, 127.4, 130.3, 132.0; u 28.6, 41.9, 45.9, 128.7, 131.7, 133.8, 137.3, 140.5, 142.9, 166.7; IR 1718 $cm^{-1}$; HRMS (ESI) m/z calcd for $C_{20}H_{24}NO_4S$ ($[M+H]^+$) 374.1426, found 374.1424.

Example 6: 2-((2,4,6-Trimethylphenyl)sulfonyl)-1,2,3,4-tetrahydroisoquinoline-6-carboxylic Acid (2c)

The above methyl ester (146 mg, 0.391 mmol) were reacted according the protocol in Example 2 to afford the carboxylic acid product as a sparingly soluble white solid (137 mg, 0.381 mmol, 97% yield), which was filtered, washed with water, dried under vacuum and used without further purification. Mp=222-233° C.; $R_f$=0.55 (10% MeOH and 2% AcOH in $CH_2Cl_2$); $^1$H NMR (400 MHz, DMSO-d6) δ 2.28 (s, 3H), 2.55 (s, 6H), 2.87 (t, J=5.6 Hz, 2H), 3.43 (t, J=5.6 Hz, 2H), 4.36 (s, 2H), 7.08 (s, 2H), 7.31 (d, J=7.6 Hz, 1H), 7.71-7.73 (m, 2H); $^{13}$C NMR (101 MHz, DMSO-d6, APT pulse sequence) δ d 20.5, 22.3, 126.8, 126.9, 129.9, 131.9; u 27.8, 41.6, 45.5, 129.2, 133.8, 137.2, 139.6, 142.6, 167.1; IR 1683 $cm^{-1}$; HRMS (ESI) m/z calcd for $C_{19}H_{22}NO_4S$ ($[M+H]^+$) 360.1264, found 360.1270.

Conversion of Carboxylic Acids 2a-2c to the Acid Chlorides

Example 7: 2-Tosyl-1,2,3,4-tetrahydroisoquinoline-6-carbonyl chloride

The carboxylic acid 2a (145 mg, 0.438 mmol) was dissolved in thionyl chloride (0.95 mL, 13.13 mmol, 30 equiv) and heated at 65° C. for 4 h. Excess thionyl chloride was removed in vacuo and the residue azeotropically dried with toluene (3×5 mL) to afford the acid chloride as a white solid (147 mg, 0.420 mmol, 96% yield), which was used without further purification. $^1$H NMR (400 MHz, $CDCl_3$) δ 2.36 (s, 3H), 2.94 (t, J=5.9 Hz, 2H), 3.32 (t, J=5.9 Hz, 2H), 4.25 (s, 2H), 7.11 (d, J=8.2 Hz, 1H), 7.25-7.30 (m, 2H), 7.63-7.69 (m, 2H), 7.77-7.85 (m, 2H).

Example 8: 2-((4-Ethylphenyl)sulfonyl)-1,2,3,4-tetrahydroisoquinoline-6-carbonyl chloride The carboxylic acid 2b (303 mg, 0.878 mmol) was reacted according the protocol in Example 7 to afford the acid chloride as a white solid (322 mg, 0.860 mmol, 98% yield), which was used without further purification. $^1$H NMR (400 MHz, CDCl$_3$) δ 1.19 (t, J=7.6 Hz, 3H), 2.65 (q, J=7.6 Hz, 2H), 2.95 (t, J=5.9 Hz, 2H), 3.33 (t, J=5.9 Hz, 2H), 4.25 (s, 2H), 7.11 (d, J=8.2 Hz, 1H), 7.27-7.32 (m, 2H), 7.65-7.71 (m, 2H), 7.77-7.85 (m, 2H).

Example 9: 2-(Mesitylsulfonyl)-1,2,3,4-tetrahydroisoquinoline-6-carbonyl chloride The carboxylic acid 2c (38 mg, 0.106 mmol) was reacted according the protocol in Example 7 to afford the acid chloride as a white solid (39 mg, 0.103 mmol, 98% yield), which was used without further purification. $^1$H NMR (400 MHz, CDCl$_3$) δ 2.31 (s, 3H), 2.63 (s, 6H), 2.95 (t, J=6.0 Hz, 2H), 3.493 (t, J=6.0 Hz, 2H), 4.43 (s, 2H), 6.97 (s, 2H), 7.21 (d, J=8.0 Hz, 1H), 7.88 (s, 1H), 7.90 (d, J=8.4 Hz, 1H).

General Amine Alkylation Procedure for the Synthesis of the Aminoacetonitrile Precursors.

The aminoacetonitrile precursors are synthesized according to the protocol described in Ruchelman, A. L.; Houghton, P. J.; Zhou, N.; Liu, A.; Liu, L. F.; LaVoie, E. J. 5-(2-Aminoethyl) dibenzo[c,h][1,6]naphthyridin-6-ones: Variation of N-Alkyl Substituents Modulates Sensitivity to Efflux Transporters Associated with Multidrug Resistance *J. Med. Chem.* 2005, 48, 792-804, incorporated herein by reference in its entirety for any and all purposes. Thus, the appropriate secondary amine is combined with chloroacetonitrile (1.1 equiv.), K$_2$CO$_3$ (2.0 equiv.) and potassium iodide (1.0 equiv.) in acetonitrile (2.5 mL/mmol of secondary amine). The reaction is stirred at room temperature ("rt", about 21° C.) for 13-16 h, diluted with aqueous saturated Na$_2$CO$_3$ (50 mL) and extracted with ether (3×30 mL). The combined organics were washed with brine and dried with Na$_2$SO$_4$. The solvent was removed in vacuo and the residue purified by silica gel chromatography to afford the necessary aminoacetonitrile precursors. Select representative synthesis of such aminoacetonitrile precursors are provided in Examples 10-13 below for the synthesis of aminoacetonitrile precursors to diamine fragments 4a-4d.

Example 10: 2-(Benzyl(tert-butyl)amino)acetonitrile

To a solution of N-benzyl-tert-butylamine (930 mg, 5.70 mmol) in MeCN (15 mL) was added K$_2$CO$_3$ (1,575 mg, 11.40 mmol, 2 equiv), potassium iodide (946 mg, 5.70 mmol, 1 equiv) and chloroacetonitrile (1,720 mg, 22.79 mmol, 4 equiv). The reaction was heated at 75° C. for 16 h, cooled to rt and partitioned between water (150 mL) and ethyl ether (3×75 mL). The combined organic layers were washed with brine (50 mL), dried (Na$_2$SO$_4$), adsorbed onto celite and purified by silica gel chromatography to afford the nitrile product as a colorless oil (846 mg, 4.18 mmol, 73% yield). R$_f$=0.49 (10% EtOAc/hexanes); $^1$H NMR (400 MHz, CDCl$_3$) δ 1.29 (s, 9H), 3.43 (s, 2H), 3.82 (s, 2H), 7.23-7.28 (m, 1H), 7.29-7.36 (complex, 4H); $^{13}$C NMR (101 MHz, CDCl$_3$, APT pulse sequence) δ d 27.4, 127.5, 128.5, 128.6; u 35.7, 51.4, 55.2, 118.0, 138.9; IR 2975, 1454, 1366, 1202 cm$^{-1}$; HRMS (ESI) m/z calcd for C$_{13}$H$_{19}$N$_2$ ([M+H]$^+$) 203.1543, found 203.1536.

Example 11: 2-((4-Fluorobenzyl)(tert-butyl)amino)acetonitrile

N-(4-Fluorobenzyl)-tert-butylamine (900 mg, 4.97 mmol) was reacted according to the protocol in Example 10 to afford the nitrile product as a colorless oil (1,038 mg, 4.71 mmol, 95% yield). R$_f$=0.49 (10% EtOAc/hexanes); $^1$H NMR (400 MHz, CDCl$_3$) δ 1.29 (s, 9H), 3.42 (s, 2H), 3.80 (s, 2H), 7.00 (t, J=8.8 Hz, 2H), 7.31 (dd, J=5.6, 8.8 Hz, 2H); $^{13}$C NMR (101 MHz, CDCl$_3$, APT pulse sequence) δ d 27.4, 115.5 (d, J=21.5 Hz), 130.1 (d, J=8.0 Hz); u 35.6, 50.7, 55.3, 117.9, 134.5, 162.3 (d, J=246 Hz); IR 2975, 1604, 1508, 1367, 1219 cm$^{-1}$; HRMS (ESI) m/z calcd for C$_{13}$H$_{18}$FN$_2$ ([M+H]$^+$) 221.1449, found 221.1438.

Example 12: 2-((4-Chlorobenzyl)(tert-butyl)amino)acetonitrile

N-(4-Chlorobenzyl)-tert-butylamine (700 mg, 3.54 mmol) was reacted according to the protocol in Example 10 to afford the nitrile product as a white solid (685 mg, 2.89 mmol, 82% yield). Mp=65-67° C.; R$_f$=0.49 (10% EtOAc/hexanes); $^1$H NMR (400 MHz, CDCl$_3$) δ 1.27 (s, 9H), 3.41 (s, 2H), 3.78 (s, 2H), 7.27 (s, 4H); $^{13}$C NMR (101 MHz, CDCl$_3$, APT pulse sequence) δ d 27.2, 128.6, 129.8; u 35.6, 50.7, 55.2, 117.7, 133.0, 137.4; IR 2975, 1597, 1490, 1368, 1201 cm$^{-1}$; HRMS (ESI) m/z calcd for C$_{13}$H$_{18}$ClN$_2$ ([M+H]$^+$) 237.1153, found 237.1141.

Example 13: 2-((4-Bromobenzyl)(tert-butyl)amino)acetonitrile

N-(4-Bromobenzyl)-tert-butylamine (920 mg, 3.80 mmol) was reacted according to the protocol in Example 10 to afford the nitrile product as a white solid (906 mg, 3.22 mmol, 85% yield). Mp=64-66° C.; R$_f$=0.49 (10% EtOAc/hexanes); $^1$H NMR (400 MHz, CDCl$_3$) δ 1.26 (s, 9H), 3.40 (s, 2H), 3.76 (s, 2H), 7.21 (d, J=8.4 Hz, 2H), 7.42 (d, J=8.0 Hz, 2H); $^{13}$C NMR (101 MHz, CDCl$_3$, APT pulse sequence) δ d 27.2, 130.1, 131.5; u 35.6, 50.7, 55.1, 117.6, 121.1, 137.9; IR 2976, 1592, 1485, 1366, 1203 cm$^{-1}$; HRMS (ESI) m/z calcd for C$_{13}$H$_{18}$BrN$_2$ ([M+H]$^+$) 281.0648, found 281.0644.

General Reduction Procedure for the Synthesis of the Diamine Fragments.

The diamine fragments were synthesized according to the protocol described in Ruchelman, A. L.; Houghton, P. J.; Zhou, N.; Liu, A.; Liu, L. F.; LaVoie, E. J. 5-(2-Aminoethyl) dibenzo[c,h][1,6]naphthyridin-6-ones: Variation of N-Alkyl Substituents Modulates Sensitivity to Efflux Transporters Associated with Multidrug Resistance *J. Med. Chem.* 2005, 48, 792-804, incorporated herein by reference in its entirety for any and all purposes. Thus, to a solution of the appropriate aminoacetonitrile precursor in THF or ether was added lithium aluminum hydride (3.5 M solution in THF, 1.1 equiv.). The reaction was stirred for 13-16 h, carefully quenched with EtOAc then water, acidified with aqueous HCl (2 M) and extracted with EtOAc (3×30 mL). The pH of the aqueous layer was adjusted to >8 with aqueous NaOH (2 M) and extracted with EtOAc (3×30 mL). The combined organics were dried with Na2SO4 and the solvent removed in vacuo to afford the diamine fragments which were used without further purification.

Example 14: Exemplary Diamine Synthesis of N¹-(4-bromobenzyl)-N¹-isopropylethane-1,2-diamine

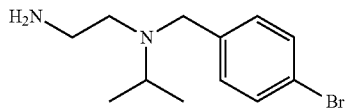

2-((4-bromobenzyl)(isopropyl)amino)acetonitrile (459 mg, 1.72 mmol) was reacted according to the general reduction procedure described above in ether to afford the diamine (384 mg, 1.42 mmol, 82% yield) as a light yellow oil. $R_f$=0.62 (10% MeOH, 1% Et3N in CH2Cl2); $^1$H NMR (400 MHz, CDCl$_3$) δ 1.01 (d, J=6.4 Hz, 6H), 2.47 (t, J=6.0 Hz, 2H), 2.61 (t, J=6.0 Hz, 2H), 2.89 (sept, J=6.4 Hz, 1H), 3.50 (s, 2H), 7.21 (d, J=8.8 Hz, 2H), 7.41 (d, J=8.4 Hz, 2H); $^{13}$C NMR (101 MHz, CDCl$_3$) δ d 17.8 (×2), 49.8, 130.0 (×2), 131.1 (×2); u 40.2, 52.3, 53.7, 120.2, 140.3; IR (neat) 2963, 1485 cm$^{-1}$; HRMS (ESI) m/z calcd for $C_{12}H_{20}BrN_2$ ([M+H]$^+$), 271.0810, found 271.0827.

Representative Synthesis of Compounds of the Present Technology.

Representative syntheses are provided below. Notably, the synthesis of comparative compound 1a is also provided, where 1a was later assayed with representative compounds of the present technology.

Example 15: Comparative compound N-(2-(Benzyl (isopropyl)amino)ethyl)-N-methyl-4-((N,4-dimethyl-phenylsulfonamido)methyl)benzamide (1a)

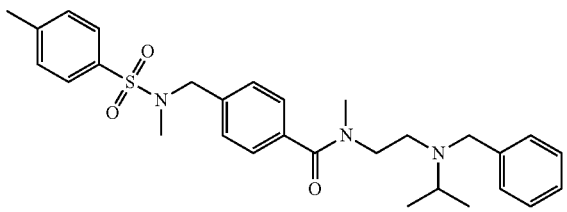 [SMILES: Cc1ccc(S(=O)(=O)N(C)Cc2ccc(C(=O)N(C)CCN(Cc3ccccc3)C(C)C)cc2)cc1]

To a solution of N-(2-(benzyl(isopropyl)amino)ethyl)-4-(((4-methylphenyl)sulfonamido) methyl)benzamide (41 mg, 0.085 mmol) in DMF (1 mL) was added sodium hydride, 60% dispersion in mineral oil (10 mg, 0.256 mmol, 3 equiv). The reaction was stirred for 10 min at rt and methyl iodide (30 mg, 0.215 mmol, 2.5 equiv) was added. The reaction was stirred at rt for 17 h and partitioned between aqueous NaHCO$_3$ and CH$_2$Cl$_2$. The organics were separated and the aqueous layer extracted with CH$_2$Cl$_2$ (3×5 mL) and the combined organic layers were dried (Na$_2$SO$_4$), concentrated and purified by silica gel chromatography to afford 1a as a light yellow oil (36 mg, 0.071 mmol, 83% yield). $R_f$=0.49 (75% EtOAc/hexanes); $^1$H NMR (400 MHz, CDCl$_3$) (ca. 1:1 mixture of rotamers) δ 0.92 (d, J=6.4 Hz, 3H), 1.06 (d, J=6.4 Hz, 3H), 2.46 (s, 3H), 2.50 (t, J=7.2 Hz, 1H), 2.54 (s, 1.5H), 2.59 (s, 1.5H), 2.73 (m, 1.5H), 2.85 (s, 1.5H), 2.93 (s, 1.5H), 3.04 (m, 0.5H), 4.14 (m, 1H), 3.41 (s, 1H), 3.49 (t, J=6.0 Hz, 1H), 3.63 (s, 1H), 4.13 (d, J=3.6 Hz, 2H), 7.19-7.37 (complex, 11H), 7.73 (d, J=8.0 Hz, 2H); $^{13}$C NMR (101 MHz, CDCl$_3$, APT pulse sequence) (mixture of rotomers) δ d 17.9, 21.5, 33.6, 34.3, 34.5, 38.6, 49.8, 50.5, 126.7, 126.9, 127.0, 127.3, 127.5, 128.2, 128.4, 128.7, 129.8; u 46.9, 47.1, 47.9, 51.0, 53.9, 54.6, 134.4, 136.4, 136.5, 136.9, 137.0, 140.4, 140.9, 143.6, 170.7, 171.5; IR 2964, 2928, 1629 cm$^{-1}$; HRMS (ESI) m/z calcd for $C_{29}H_{38}N_3O_3S$ ([M+H]$^+$) 508.2628, found 508.2629; HPLC purity=97.4%.

Example 16: N-(2-(tert-butyl(4-methoxybenzyl) amino)ethyl)-2-tosyl-1,2,3,4-tetrahydroisoquinoline-6-carboxamide (1b)

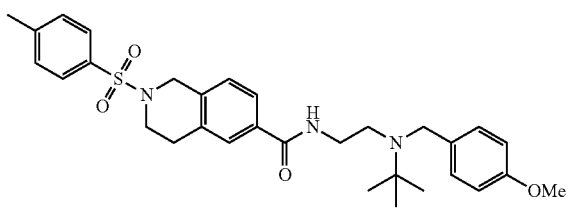 [SMILES: COc1ccc(CN(CCNC(=O)c2ccc3c(c2)CCN(S(=O)(=O)c2ccc(C)cc2)C3)C(C)(C)C)cc1]

To a solution of 2-tosyl-1,2,3,4-tetrahydroisoquinoline-6-carboxylic acid 2a (100 mg, 0.30 mmol), diamine fragment 4e (71 mg, 0.30 mmol) and diisopropylethylamine (0.16 mL, 0.90 mmol, 3.0 equiv) in DMF (3 mL) was added HATU (125 mg, 0.33 mmol, 1.1 equiv). The reaction was stirred for 18 h at rt and all solvents removed in vacuo. The residue was purified by mass-directed, reverse phase preparative HPLC to afford 1b (131 mg, 0.24 mmol, 79% yield). $^1$H NMR (400 MHz, CDCl$_3$) δ 1.15 (s, 9H), 2.42 (s, 3H), 2.80 (dd, J=5.1, 6.6 Hz, 2H), 2.95 (t, J=5.9 Hz, 1H), 3.11-3.23 (m, 2H), 3.36 (t, J=5.9 Hz, 2H), 3.61 (s, 2H), 3.61 (s, 3H), 4.26 (s, 2H), 6.17 (t, J=5.3 Hz, 1H), 6.72-6.77 (m, 2H), 7.03 (d, J=8.0 Hz, 1H), 7.20-7.25 (m, 3H), 7.31-7.37 (m, 3H), 7.67-7.80 (m, 2H); $^{13}$C NMR (101 MHz, CDCl$_3$) δ 21.7, 27.5, 29.0, 40.2, 43.7, 47.7, 49.9, 54.7, 55.3, 55.6, 114.0, 124.5, 126.5, 127.8, 127.9, 129.2, 129.9, 133.2, 133.5, 134.6, 134.9, 144.0, 158.5, 166.8; HRMS (ESI) m/z calcd for $C_{31}H_{40}N_3O_4S$ ([M+H]$^+$), 550.2740, found 550.2719; HPLC purity=97.2%.

Example 17: N-(2-(Benzyl(isopropyl)amino)ethyl)-2-(mesitylsulfonyl)-1,2,3,4-tetrahydroisoquinoline-6-carboxamide (1c)

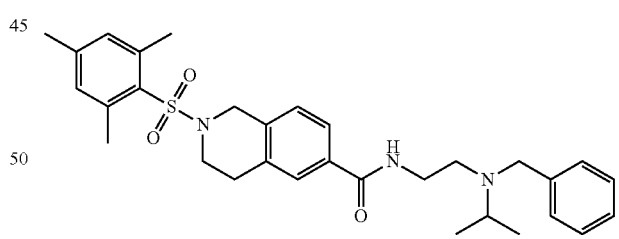

To a solution of 2-(mesitylsulfonyl)-1,2,3,4-tetrahydroisoquinoline-6-carbonyl chloride (20 mg, 0.054 mmol) in CH$_2$Cl$_2$ (3 mL) was added diamine fragment 3a (10 mg, 0.054 mmol) and triethylamine (0.019 mL, 0.14 mmol, 2.6 equiv). The reaction was stirred for 48 h at rt, aqueous, saturated sodium bicarbonate solution (2 mL) was added and all solvents removed in vacuo. The residue was extracted with a solution of CH$_2$Cl$_2$:MeOH (5:1, 6 mL). The filtrate was dried (Na$_2$SO$_4$), evaporated and purified by mass-directed, reverse phase preparative HPLC to afford 1c (9 mg, 0.017 mmol, 31% yield). $^1$H NMR (400 MHz, CDCl$_3$) δ 1.00 (d, J=6.6 Hz, 6H), 2.24 (s, 3H), 2.57 (s, 6H), 2.61 (t, J=5.8 Hz, 2H), 2.83 (t, J=5.9 Hz, 2H), 2.94 (sep, J=6.6 Hz, 1H), 3.29 (q, J=5.0 Hz, 2H), 3.41 (t, J=5.9 Hz, 2H), 3.49 (s, 2H), 4.33 (s, 2H), 6.47 (br s, 1H), 6.90 (s, 2H), 7.03 (d, J=8.0 Hz, 1H), 7.15-7.30 (m, 6H), 7.39 (s, 1H); $^{13}$C NMR (101 MHz, CDCl$_3$) δ 18.0, 21.0, 22.9, 28.7, 37.5, 41.9, 45.7, 47.8, 49.7, 53.7, 124.4, 126.6, 127.0, 127.9, 128.5, 128.6, 131.6, 132.0, 133.3, 133.8, 135.4, 140.6, 140.8, 142.9, 166.7; IR 3378, 2965, 1648, 1544 cm$^{-1}$; HRMS (ESI) m/z calcd for C$_{31}$H$_{39}$N$_3$O$_3$S ([M+H]$^+$), 534.2790, found 534.2804; HPLC purity=98.7%.

Example 18: N-(2-((4-Fluorobenzyl)(isopropyl) amino)ethyl)-2-tosyl-1,2,3,4-tetrahydroisoquinoline-6-carboxamide (1d)

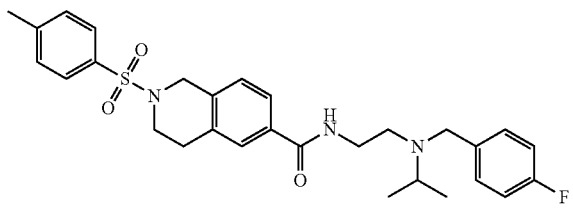 [SMILES: Cc1ccc(S(=O)(=O)N2CCc3cc(C(=O)NCCN(Cc4ccc(F)cc4)C(C)C)ccc3C2)cc1]

2-Tosyl-1,2,3,4-tetrahydroisoquinoline-6-carbonyl chloride (20 mg, 0.054 mmol) and diamine fragment 3b (11 mg, 0.054 mmol) were reacted according the protocol in Example 17 to afford 1d (15 mg, 0.028 mmol, 52% yield). $^1$H NMR (400 MHz, DMSO-d$_6$) δ 0.96 (d, J=6.4 Hz, 6H), 2.39 (s, 3H), 2.51 (m, 2H), 2.82-2.90 (m, 3H), 3.22 (m, 2H), 3.29 (t, J=6.4 Hz, 2H), 3.54 (s, 2H), 4.21 (s, 2H), 7.06 (t, J=8.8 Hz, 2H), 7.23 (d, J=8.4 Hz, 1H), 7.36 (dd, J=6.4, 8.8 Hz, 2H), 7.43 (d, J=8.0 Hz, 2H), 7.56 (m, 2H), 7.72 (d, J=8.4 Hz, 2H); $^{13}$C NMR (101 MHz, DMSO-d$_6$) δ 17.9, 21.0, 28.0, 40.4, 43.4, 47.2, 48.4, 49.3, 53.0, 114.7 (d, J=21.1 Hz), 124.7, 126.4, 127.45, 127.49, 129.9 130.0, 132.90, 132.96, 132.99, 134.6, 137.0 (d, J=2.8 Hz), 143.7, 161.0 (d, J=242.3 Hz), 165.6; IR 2966, 1649, 1508 cm$^{-1}$; HRMS (ESI) m/z calcd for C$_{29}$H$_{35}$FN$_3$O$_3$S ([M+H]$^+$), 524.2383, found 524.2401; HPLC purity=97.0%.

Example 19: N-(2-((4-Chlorobenzyl)(isopropyl) amino)ethyl)-2-tosyl-1,2,3,4-tetrahydroisoquinoline-6-carboxamide (1e)

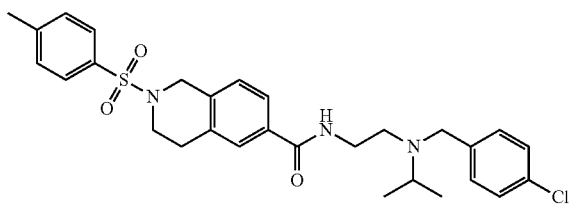 [SMILES: Cc1ccc(S(=O)(=O)N2CCc3cc(C(=O)NCCN(Cc4ccc(Cl)cc4)C(C)C)ccc3C2)cc1]

2-Tosyl-1,2,3,4-tetrahydroisoquinoline-6-carbonyl chloride (20 mg, 0.054 mmol) and diamine fragment 3c (12 mg, 0.054 mmol) were reacted according the protocol in Example 17 to afford 1e (13 mg, 0.024 mmol, 45% yield). $^1$H NMR (400 MHz, DMSO-d$_6$) δ 0.95 (d, J=6.4 Hz, 6H), 2.31 (s, 3H), 2.55 (m, 2H), 2.85 (m, 2H), 3.24-3.28 (m, 4H), 3.41 (s, 2H), 4.17 (s, 2H), 6.97 (d, J=8.0 Hz, 1H), 7.07-7.12 (complex, 4H), 7.15 (s, 1H), 7.19 (m, 1H), 7.22 (d, J=8.0 Hz, 2H), 7.31 (br s, 1H), 7.62 (d, J=8.4 Hz, 2H); $^{13}$C NMR (101 MHz, DMSO-d$_6$) δ 17.9, 21.0, 28.0, 40.4, 43.4, 47.2, 48.6, 49.5, 53.0, 124.7, 126.4, 127.4, 127.5, 127.9, 129.86, 129.95, 130.2, 130.9, 132.9, 133.0, 134.6, 140.1 143.6, 165.6; IR 2966, 1647, 1543, 1491 cm$^{-1}$; HRMS (ESI) m/z calcd for C$_{29}$H$_{35}$ClN$_3$O$_3$S ([M+H]$^+$), 540.2088, found 540.2104; HPLC purity=100.0%.

Example 20: N-(2-((4-Bromobenzyl)(isopropyl) amino)ethyl)-2-tosyl-1,2,3,4-tetrahydroisoquinoline-6-carboxamide (1f)

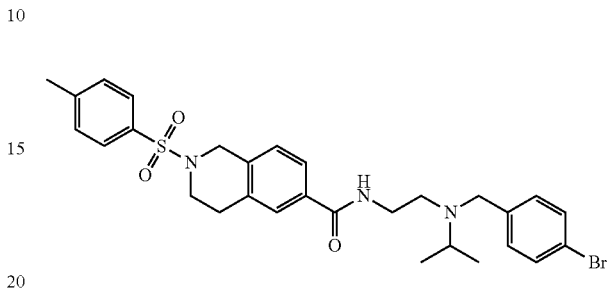

2-Tosyl-1,2,3,4-tetrahydroisoquinoline-6-carbonyl chloride (20 mg, 0.054 mmol) and diamine fragment 3d (15 mg, 0.054 mmol) were reacted according the protocol in Example 17 to afford 1f (18 mg, 0.30 mmol, 56% yield). $^1$H NMR (400 MHz, CDCl$_3$) δ 0.98 (d, J=6.4 Hz, 6H), 2.35 (s, 3H), 2.58 (t, J=5.6 Hz, 2H), 2.88-2.94 (m, 3H), 3.26-3.31 (m, 4H), 3.42 (s, 2H), 4.21 (s, 2H), 6.39 (br s, 1H), 7.01 (d, J=8.0 Hz, 1H), 7.08 (d, J=8.4 Hz, 1H), 7.22-7.28 (complex, 5H), 7.34 (s, 1H), 7.66 (d, J=8.4 Hz, 2H); $^{13}$C NMR (101 MHz, CDCl$_3$) δ 18.1, 21.6, 29.0, 37.8, 43.7, 47.6, 48.2, 49.9, 53.2, 120.7, 124.4, 126.6, 127.75, 127.82, 129.9, 130.4, 131.6, 133.2, 133.3, 133.7, 135.1, 139.9 144.0, 166.9; IR 2965, 1646, 1541, 1486 cm$^{-1}$; HRMS (ESI) m/z calcd for C$_{29}$H$_{34}$BrN$_3$O$_3$S ([M+H]$^+$), 586.1562, found 586.1585; HPLC purity=94.6%.

Example 21: N-(2-((4-Bromobenzyl)(isopropyl) amino)ethyl)-2-((4-ethylphenyl)sulfonyl)-1,2,3,4-tetrahydroisoquinoline-6-carboxamide (1g)

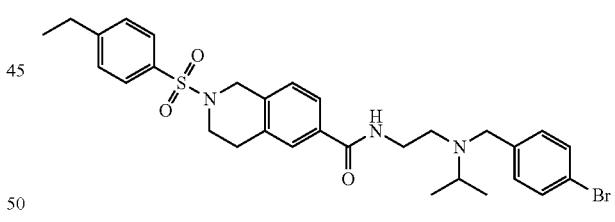

2-((4-Ethylphenyl)sulfonyl)-1,2,3,4-tetrahydroisoquinoline-6-carbonyl chloride (160 mg, 0.44 mmol) and diamine fragment 3d (119 mg, 0.44 mmol) were reacted according the protocol in Example 17 to afford 1g (122 mg, 0.21 mmol, 47% yield). $^1$H NMR (400 MHz, DMSO-d$_6$) δ 0.95 (d, J=6.8 Hz, 6H), 1.15 (t, J=7.6 Hz, 3H), 2.55 (t, J=6.0 Hz, 2H), 2.61 (q, J=7.6 Hz, 2H), 2.83-2.90 (m, 3H), 3.22-3.28 (m, 4H) 3.40 (s, 2H), 4.18 (s, 2H), 6.52 (br s, 1H), 6.99 (d, J=8.0 Hz, 1H), 7.07 (d, J=8.4 Hz, 1H) 7.21-7.27 (complex, 5H), 7.33 (s, 1H), 7.65 (d, J=8.4 Hz, 2H); $^{13}$C NMR (101 MHz, DMSO-d$_6$) δ 15.0, 17.8, 27.98, 28.03, 40.4, 43.4, 47.2, 48.6, 49.5, 53.1, 119.3, 124.7, 126.3, 127.47, 127.55, 128.7, 130.3, 130.8, 132.92, 132.93, 133.1, 134.6, 140.5 149.5, 165.6; IR 2965, 1646, 1541, 1486 cm$^{-1}$; HRMS (ESI) m/z calcd for C$_{30}$H$_{36}$BrN$_3$O$_3$S ([M+H]$^+$), 600.1719, found 600.1740; HPLC purity=98.1%.

Example 22: N-(2-(Benzyl(tert-butyl)amino)ethyl)-2-tosyl-1,2,3,4-tetrahydroisoquinoline-6-carboxamide (1h)

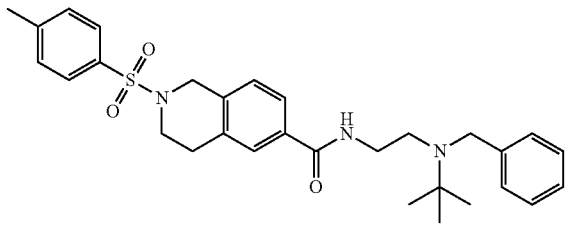 [SMILES: Cc1ccc(S(=O)(=O)N2CCc3cc(C(=O)NCCN(Cc4ccccc4)C(C)(C)C)ccc3C2)cc1]

2-Tosyl-1,2,3,4-tetrahydroisoquinoline-6-carbonyl chloride (20 mg, 0.054 mmol) and diamine fragment 4a (11 mg, 0.054 mmol) were reacted according the protocol in Example 17 to afford 1h (26 mg, 0.049 mmol, 91% yield). $^1$H NMR (400 MHz, CDCl$_3$) δ 1.10 (s, 9H), 2.36 (s, 3H), 2.76 (t, J=6.0 Hz, 2H), 2.89 (t, J=6.0 Hz, 2H), 3.12 (q, J=5.6 Hz, 2H), 3.30 (t, J=6.0 Hz, 2H), 3.64 (s, 2H), 4.21 (s, 2H), 6.22 (br s, 1H), 6.98 (d, J=8.0 Hz, 1H), 7.09 (m, 1H), 7.16-7.22 (m, 3H), 7.27-7.29 (complex, 5H), 7.66 (d, J=8.4 Hz, 2H); $^{13}$C NMR (101 MHz, CDCl$_3$) δ 21.6, 27.5, 28.9, 39.9, 43.7, 47.6, 50.1, 55.2, 55.6, 124.5, 126.5, 126.8, 127.7, 127.8, 127.9, 128.5, 129.9, 133.2, 133.36, 133.42, 134.9, 142.9, 143.9, 166.7; IR 2989, 1628, 1538, 1497 cm$^{-1}$; HRMS (ESI) m/z calcd for C$_{30}$H$_{37}$N$_3$O$_3$S ([M+H]$^+$), 520.2634, found 520.2650; HPLC purity=97.5%.

Example 23: N-(2-(Benzyl(tert-butyl)amino)ethyl)-((4-ethylphenyl)sulfonyl)-1,2,3,4-tetrahydroisoquinoline-6-carboxamide (1i)

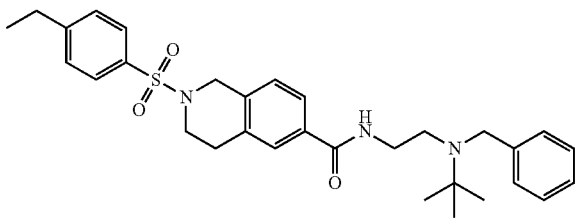 [SMILES: CCc1ccc(S(=O)(=O)N2CCc3cc(C(=O)NCCN(Cc4ccccc4)C(C)(C)C)ccc3C2)cc1]

2-((4-Ethylphenyl)sulfonyl)-1,2,3,4-tetrahydroisoquinoline-6-carbonyl chloride (160 mg, 0.44 mmol) and diamine fragment 4a (91 mg, 0.44 mmol) were reacted according the protocol in Example 17 to afford 1i (66 mg, 0.12 mmol, 28% yield). $^1$H NMR (400 MHz, CDCl$_3$) δ 1.11 (s, 9H), 1.20 (t, J=7.6 Hz, 3H), 2.67 (q, J=7.6 Hz, 2H), 2.77 (t, J=6.1 Hz, 2H), 2.90 (t, J=5.9 Hz, 2H), 3.12 (q, J=5.9 Hz, 2H), 3.31 (t, J=5.9 Hz, 2H), 3.65 (s, 2H), 4.21 (s, 2H), 6.37 (br s, 1H), 7.00 (d, J=8.0 Hz, 1H), 7.07-7.11 (m, 1H), 7.16-7.21 (m, 2H), 7.24-7.27 (m, 1H), 7.29-7.33 (m, 5H), 7.67-7.71 (m, 2H); $^{13}$C NMR (101 MHz, CDCl$_3$) δ 15.0, 27.3, 28.7, 28.8, 39.9, 40.9, 43.6, 47.7, 50.0, 55.1, 124.5, 126.4, 126.6, 127.6, 127.76, 127.81, 128.3, 128.6, 133.1, 133.2, 134.7, 142.8, 149.9, 166.6; IR 2968, 1645, 1540, 1494 cm$^{-1}$; HRMS (ESI) m/z calcd for C$_{31}$H$_{39}$N$_3$O$_3$S ([M+H]$^+$), 534.2790, found 534.2801; HPLC purity=94.7%.

Example 24: N-(2-((4-Fluorobenzyl)(tert-butyl)amino)ethyl)-2-tosyl-1,2,3,4-tetrahydroisoquinoline-6-carboxamide (1j)

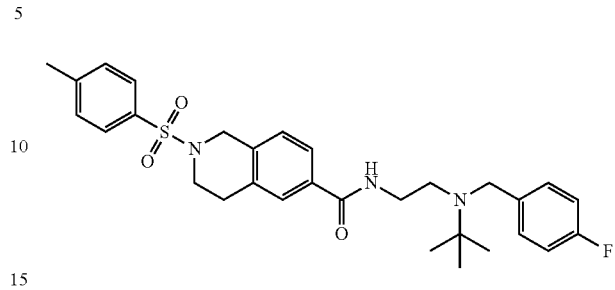

2-Tosyl-1,2,3,4-tetrahydroisoquinoline-6-carbonyl chloride (20 mg, 0.054 mmol) and diamine fragment 4b (12 mg, 0.054 mmol) were reacted according the protocol in Example 17 to afford 1j (28 mg, 0.052 mmol, 96% yield). $^1$H NMR (400 MHz, CDCl$_3$) δ 1.08 (s, 9H), 2.35 (s, 3H), 2.73 (t, J=6.1 Hz, 2H), 2.87 (t, J=5.9 Hz, 2H), 3.10 (q, J=5.6 Hz, 2H), 3.29 (t, J=5.9 Hz, 2H), 3.58 (s, 2H), 4.20 (s, 2H), 6.10 (br s, 1H), 6.77-6.84 (m, 2H), 6.97 (d, J=8.0 Hz, 1H), 7.18-7.28 (m, 6H), 7.64-7.67 (m, 2H); $^{13}$C NMR (101 MHz, CDCl$_3$) δ 21.5, 27.4, 28.8, 40.1, 43.6, 47.5, 50.0, 54.5, 55.5, 115.2 (d, J=21.2 Hz), 124.3, 126.4, 127.6, 127.7, 129.3 (d, J=8.0 Hz), 129.8, 133.2, 133.3, 133.5, 135.0, 138.3 (d, J=4.0 Hz), 143.9, 161.6 (d, J=245.4 Hz), 166.7; IR 2970, 1643, 1541, 1506 cm$^{-1}$; HRMS (ESI) m/z calcd for C$_{30}$H$_{36}$FN$_3$O$_3$S ([M+H]$^+$), 538.2540, found 538.2554; HPLC purity=96.3%.

Example 25: N-(2-((4-Fluorobenzyl)(tert-butyl)amino)ethyl)-2-(mesitylsulfonyl)-1,2,3,4-tetrahydroisoquinoline-6-carboxamide (1k)

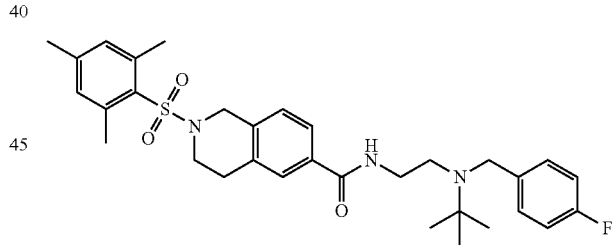

2-(mesitylsulfonyl)-1,2,3,4-tetrahydroisoquinoline-6-carbonyl chloride (20 mg, 0.054 mmol) and diamine fragment 4b (12 mg, 0.054 mmol) were reacted according the protocol in Example 17 to afford 1k (14 mg, 0.024 mmol, 45% yield). $^1$H NMR (400 MHz, CDCl$_3$) δ 1.08 (s, 9H), 2.35 (s, 3H), 2.73 (t, J=6.1 Hz, 2H), 2.87 (t, J=5.9 Hz, 2H), 3.10 (q, J=5.6 Hz, 2H), 3.29 (t, J=5.9 Hz, 2H), 3.58 (s, 2H), 4.20 (s, 2H), 6.10 (br s, 1H), 6.77-6.84 (m, 2H), 6.97 (d, J=8.0 Hz, 1H), 7.18-7.28 (m, 6H), 7.64-7.67 (m, 2H); $^{13}$C NMR (101 MHz, CDCl$_3$) δ 21.5, 27.4, 28.8, 40.1, 43.6, 47.5, 50.0, 54.5, 55.5, 115.2 (d, J=21.2 Hz), 124.3, 126.4, 127.6, 127.7, 129.3 (d, J=8.0 Hz), 129.8, 133.2, 133.3, 133.5, 135.0, 138.3 (d, J=4.0 Hz), 143.9, 161.6 (d, J=245.4 Hz), 166.7; IR 2971, 1644, 1604, 1543 cm$^{-1}$; HRMS (ESI) m/z calcd for C$_{32}$H$_{41}$FN$_3$O$_3$S ([M+H]$^+$), 566.2853, found 566.2871; HPLC purity=99.1%.

Example 26: N-(2-((4-Chlorobenzyl)(tert-butyl)amino)ethyl)-2-tosyl-1,2,3,4-tetrahydroisoquinoline-6-carboxamide (1l)

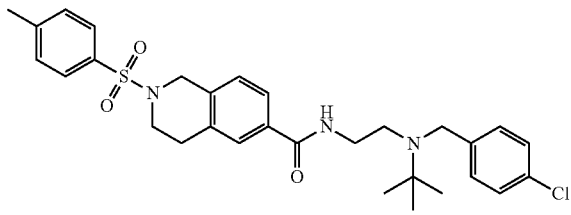 [SMILES: Cc1ccc(S(=O)(=O)N2CCc3cc(C(=O)NCCN(Cc4ccc(Cl)cc4)C(C)(C)C)ccc3C2)cc1]

2-Tosyl-1,2,3,4-tetrahydroisoquinoline-6-carbonyl chloride (20 mg, 0.054 mmol) and diamine fragment 4c (13 mg, 0.054 mmol) were reacted according the protocol in Example 17 to afford 1l (25 mg, 0.046 mmol, 85% yield). $^1$H NMR (400 MHz, CDCl$_3$) δ 1.09 (s, 9H), 2.39 (s, 3H), 2.64 (m, 2H), 2.87 (t, J=6.0 Hz, 2H), 3.04 (m, 2H), 3.28 (t, J=6.0 Hz, 2H), 3.69 (s, 2H), 4.20 (s, 2H), 7.20 (d, J=8.0 Hz, 1H), 7.31 (m, 2H), 7.39-7.45 (m, 4H), 7.53 (m, 2H), 7.71 (d, J=8.4 Hz, 2H); $^{13}$C NMR (101 MHz, CDCl$_3$) δ 21.0, 27.1, 28.0, 40.4, 43.4, 47.2, 49.9, 53.4, 54.8, 124.7, 126.3, 127.42, 127.45, 127.8, 129.3, 129.9, 130.5, 132.77, 132.84, 132.9, 134.6, 142.1, 143.6, 165.5; IR 2969, 1644, 1541 cm$^{-1}$; HRMS (ESI) m/z calcd for C$_{30}$H$_{37}$ClN$_3$O$_3$S ([M+H]$^+$), 554.2244, found 554.2261; HPLC purity=99.2%.

Example 27: N-(2-((4-Bromobenzyl)(tert-butyl)amino)ethyl)-2-tosyl-1,2,3,4-tetrahydroisoquinoline-6-carboxamide (1m)

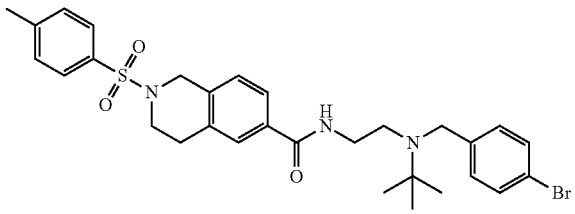 [SMILES: Cc1ccc(S(=O)(=O)N2CCc3cc(C(=O)NCCN(Cc4ccc(Br)cc4)C(C)(C)C)ccc3C2)cc1]

2-Tosyl-1,2,3,4-tetrahydroisoquinoline-6-carbonyl chloride (20 mg, 0.054 mmol) and diamine fragment 4d (15 mg, 0.054 mmol) were reacted according the protocol in Example 17 to afford 1m (7.8 mg, 0.013 mmol, 24% yield). $^1$H NMR (400 MHz, CDCl$_3$) δ 1.08 (s, 9H), 2.35 (s, 3H), 2.74 (t, J=6.0 Hz, 2H), 2.89 (t, J=5.9 Hz, 2H), 3.13 (q, J=5.8 Hz, 2H), 3.27-3.32 (m, 2H), 3.56 (s, 2H), 4.21 (s, 2H), 6.07 (br s, 1H), 7.00 (d, J=8.0 Hz, 1H), 7.11-7.20 (m, 3H), 7.23-7.30 (m, 5H), 7.64-7.68 (m, 2H); $^{13}$C NMR (101 MHz, CDCl$_3$) δ 21.6, 27.3, 28.9, 40.1, 43.6, 47.5, 50.2, 54.6, 55.6, 113.9, 124.3, 126.5, 127.6, 127.7, 129.5, 129.8, 131.5, 133.19, 133.22, 133.6, 135.0, 143.8, 166.7; IR 2980, 1652, 1521 cm$^{-1}$; HRMS (ESI) m/z calcd for C$_{30}$H$_{36}$BrN$_3$O$_3$S ([M+H]$^+$), 600.1719, found 600.1740; HPLC purity=94.1%.

Example 28: N-(2-((4-Bromobenzyl)(tert-butyl)amino)ethyl)-2-(mesitylsulfonyl)-1,2,3,4-tetrahydroisoquinoline-6-carboxamide (1n)

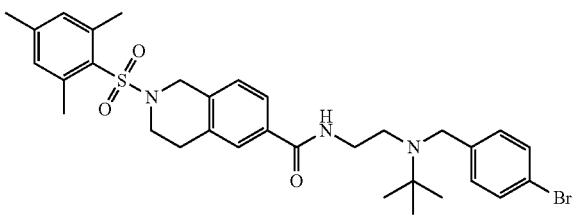 [SMILES: Cc1cc(C)c(S(=O)(=O)N2CCc3cc(C(=O)NCCN(Cc4ccc(Br)cc4)C(C)(C)C)ccc3C2)c(C)c1]

2-(mesitylsulfonyl)-1,2,3,4-tetrahydroisoquinoline-6-carbonyl chloride (20 mg, 0.054 mmol) and diamine fragment 4d (15 mg, 0.054 mmol) were reacted according the protocol in Example 17 to afford 1n (10 mg, 0.016 mmol, 29% yield). $^1$H NMR (400 MHz, CDCl$_3$) δ 1.08 (s, 9H), 2.35 (s, 3H), 2.74 (t, J=6.0 Hz, 2H), 2.89 (t, J=5.9 Hz, 2H), 3.13 (q, J=5.8 Hz, 2H), 3.27-3.32 (m, 2H), 3.56 (s, 2H), 4.21 (s, 2H), 6.07 (br s, 1H), 7.00 (d, J=8.0 Hz, 1H), 7.11-7.20 (m, 3H), 7.23-7.30 (m, 5H), 7.64-7.68 (m, 2H); $^{13}$C NMR (101 MHz, CDCl$_3$) δ 21.6, 27.3, 28.9, 40.1, 43.6, 47.5, 50.2, 54.6, 55.6, 120.3, 124.3, 126.5, 127.6, 127.7, 129.5, 129.8, 131.5, 133.21, 133.23, 133.6, 135.0, 141.9, 143.8, 166.7; IR 2972, 1647, 1533 cm$^{-1}$; HRMS (ESI) m/z calcd for C$_{30}$H$_{36}$BrN$_3$O$_3$S ([M+H]$^+$), 600.1719, found 600.1740; HPLC purity=94.1%.

Representative Biological Activity of Compounds of the Present Technology

In Vitro Assay Methods

1. Compounds and Reagents (+)-(5α,7α,8β)-N-Methyl-N-(7-(1-pyrrolidinyl)-1-oxaspiro(4.5)dec-8-yl)-benzeneacetamide (U69,593) and nor-binaltorphimine dihydrochloride (norBNI) were purchased from Sigma Aldrich. The structure of U69,593 is provided below.

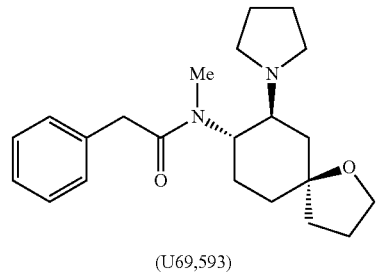 [SMILES: CN(C(=O)Cc1ccccc1)[C@H]1CC[C@@]2(CCCO2)C[C@@H]1N1CCCC1]

(U69,593)

U69,593 was prepared in ethanol as a 10 mM stock, norBNI was prepared in water as a 10 mM stock, and test compounds were prepared as 10 mM stocks in DMSO (Fisher). All compounds were then diluted to working concentrations in vehicle for each assay without exceeding 1% DMSO or ethanol concentrations. [$^{35}$S]GTPγS was purchased from PerkinElmer Life Sciences. Phospho-ERK1/2 and total ERK1/2 antibodies were purchased from Cell Signaling (Beverly, Mass.) and Li-Cor secondary antibodies (anti-rabbit IRDye800CW and anti-mouse IRDye680LT) were purchased from Li-Cor Biosciences.

2. Cell Lines and Cell Culture

Chinese hamster ovary (CHO) cells were virally transfected to express HA-tagged recombinant human kappa opioid receptors (CHO-hKOR cell line) and maintained in DMEM/F-12 media (Invitrogen) supplemented with 10% fetal bovine serum, 1% penicillin/streptomycin, and 500 µg/ml geneticin as described in Schmid, C. L.; Streicher, J. M.; Groer, C. E.; Munro, T. A.; Zhou, L.; Bohn, L. M. Functional selectivity of 6'-guanidinonaltrindole (6'-GNTI) at kappa opioid receptors in striatal neurons. *J. Biol. Chem.* 2013, 288, 22387-22398. A DiscoveRx PathHunter™ U2OS cell line expressing βarrestin2 and hKOR (U2OS-hKOR-βarrestin2-DX) was purchased from DiscoveRx Corporation (Fremont, Calif.) and maintained MEM with 10% fetal bovine serum, 1% penicillin/streptomycin, 500 µg/ml geneticin and 250 µg/ml hygromycin B. All cells were grown at 37° C. (5% CO$_2$ and 95% relative humidity).

3. Protein Coupling Assay

[$^{35}$S]GTPγS binding assay was performed following a previously published protocol (Zhou, L.; Lovell, K. M.; Frankowski, K. J.; Slauson, S. R.; Phillips, A. M. Streicher, J. M.; Stahl, E.; Schmid, C. L.; Hodder, P.; Madoux, F.; Cameron, M. D.; Prisinzano, T. E.; Aubé, J.; Bohn, L. M. *J. Biol. Chem.* 2013, 288, 36703-36716). Briefly, cells were serum starved for 1 hour and membranes were prepared. Each reaction was performed at room temperature and contained 15 μg of membrane protein, 40 μM GDP, ~0.1 nM [$^{35}$S]GTPγS and increasing concentrations of compounds in assay buffer (50 mM Tris-HCl, pH 7.4, 100 mM NaCl, 5 mM MgCl$_2$, 1 mM EDTA). Directly after the addition of test compounds, 100 nM U69,593 was added to yield a total volume of 200 μL. After 1 hour, reactions were quenched by rapid filtration through GF/B filters and radioactivity was counted with a TopCount NXT high throughput screening microplate scintillation and luminescence counter (PerkinElmer Life Sciences).

4. βArrestin2 Recruitment (DiscoveRx PathHunter™) Assay

The PathHunter™ assay was performed according to the manufacturer's protocol with slight modification and following known protocols (Schmid, C. L.; Streicher, J. M.; Groer, C. E.; Munro, T. A.; Zhou, L.; Bohn, L. M. Functional selectivity of 6'-guanidinonaltrindole (6'-GNTI) at kappa opioid receptors in striatal neurons. *J. Biol. Chem.* 2013, 288, 22387-22398; Zhou, L.; Lovell, K. M.; Frankowski, K. J.; Slauson, S. R.; Phillips, A. M. Streicher, J. M.; Stahl, E.; Schmid, C. L.; Hodder, P.; Madoux, F.; Cameron, M. D.; Prisinzano, T. E.; Aubé, J.; Bohn, L. M. Development of functionally selective, small molecule agonists at kappa opioid receptors. *J. Biol. Chem.* 2013, 288, 36703-36716). Briefly, 5,000 cells/well were plated overnight in Opti-MEM containing 1% fetal bovine serum, 1% penicillin/streptomycin. Cells were pretreated with antagonist for 15 min at 37° C. followed by the addition of 1 μM U69,593 and a 90 minute incubation at 37° C. PathHunter™ detection reagent was added and cells incubated at room temperature for 60 minutes. Chemiluminescence was detected using a SpectraMax® M5e Multimode Plate Reader (Molecular Devices). βarrestin2 recruitment assays were also performed using an imaging platform (Cellomics) to visualize translocation of a fluorescent protein tagged parrestin2 to the membrane of KOR expressing U2OS cells.

5. In-Cell Western ERK1/2 Phosphorylation

Antagonist inhibition of U69,593 induced ERK phosphorylation was determined by in-cell westerns via known protocols (Schmid, C. L.; Streicher, J. M.; Groer, C. E.; Munro, T. A.; Zhou, L.; Bohn, L. M. Functional selectivity of 6'-guanidinonaltrindole (6'-GNTI) at kappa opioid receptors in striatal neurons. *J. Biol. Chem.* 2013, 288, 22387-22398; Zhou, L.; Lovell, K. M.; Frankowski, K. J.; Slauson, S. R.; Phillips, A. M. Streicher, J. M.; Stahl, E.; Schmid, C. L.; Hodder, P.; Madoux, F.; Cameron, M. D.; Prisinzano, T. E.; Aubé, J.; Bohn, L. M. Development of functionally selective, small molecule agonists at kappa opioid receptors. *J. Biol. Chem.* 2013, 288, 36703-36716). Briefly, hKOR-CHO cells were plated in 384-well plate at 15,000 cells per well and incubated at 37° C. overnight. After an hour serum starve, cells were treated with compound followed by the addition of 100 nM U69,593 and a 10 minute incubation at 37° C. Cells were fixed, permeabilized, blocked, and stained with primary antibodies for phosphorylated ERK1/2 and total-ERK1/2 (1:300 and 1:400, respectively) at 4° C. overnight. Cells then incubated with Li-Cor secondary antibodies (anti-rabbit IRDye800CW, 1:500; anti-mouse IRDye680LT, 1:1500) and imaged with the Odyssey Infrared Imager (Li-Cor Biosciences, Lincoln, Nebr.) at 700 and 800 nm.

6. Data Analysis and Statistics

GraphPad Prism 6.01 software (GraphPad) was used to generate sigmoidal dose response curves using a three-parameter, non-linear regression analysis. All compounds were run in parallel assays in 2-4 replicates per individual experiment. All studies were performed n>3 independent experiments in multiple replicates. For determination of antagonist inhibition, each individual experiment was normalized to the percentage of maximal U69,593 stimulation. The efficacy and potency values were obtained from the averages of the nonlinear regression analysis performed on each individual curve and are reported as the mean±S.E.M.

TABLE 1

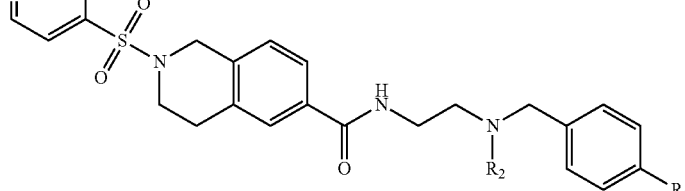

| entry/cmpd | R$^1$ | R$^2$ | R$^3$ | IC$_{50}$ (nM) ± S.E.M.$^a$ | | |
|---|---|---|---|---|---|---|
| | | | | [$^{35}$S]GTPγS | ERK | βarr2 |
| norBNI | — | — | — | 0.28 ± 0.03 | 4.6 ± 0.7 | 2.5 ± 0.3 |
| ML140 | 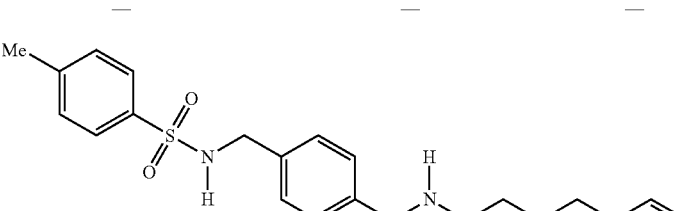 | | | 138 ± 54 | 591 ± 87 | 403 |

TABLE 1-continued

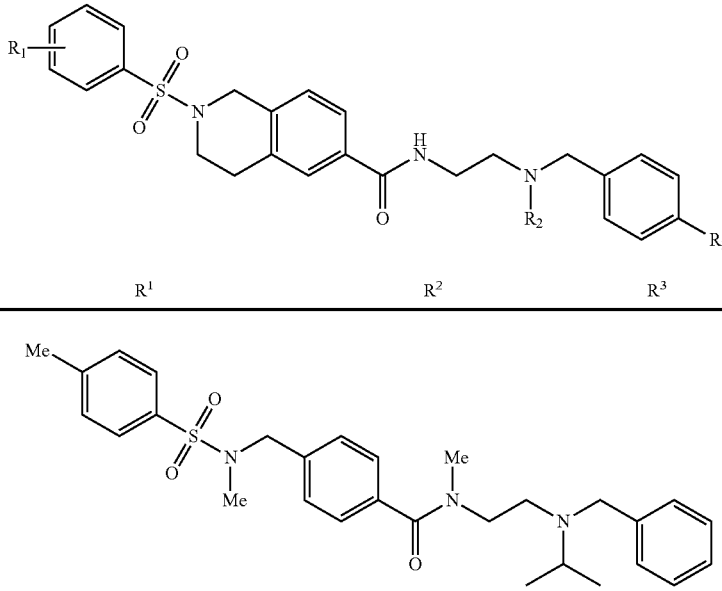

| entry/cmpd | R¹ | R² | R³ | [$^{35}$S]GTPγS | ERK | βarr2 |
|---|---|---|---|---|---|---|
| 1a | Me- | | | inactive | inactive | inactive |
| 1c | 2,4,6-Me | i-Pr | H | 113 ± 42 | 1,120 ± 110 | 930 ± 150 |
| 1d | 4-Me | i-Pr | F | 29.1 ± 7.9 | 406 ± 80 | 478 ± 110 |
| 1e | 4-Me | i-Pr | Cl | 10.0 ± 1.4 | 400 ± 87 | 392 ± 91 |
| 1f | 4-Me | i-Pr | Br | 19.7 ± 6.6 | 258 ± 93 | 388 ± 85 |
| 1g | 4-Et | i-Pr | Br | 33 ± 11 | 314 ± 56 | 350 ± 68 |
| 1h | 4-Me | tert-Bu | H | 5.28 ± 0.60 | 49.1 ± 9.7 | 103.7 ± 8.2 |
| 1i | 4-Et | tert-Bu | H | 3.41 ± 0.40 | 143 ± 23 | 186 ± 57 |
| 1j | 4-Me | tert-Bu | F | 3.7 ± 1.2 | 76 ± 24 | 104 ± 32 |
| 1k | 2,4,6-Me | tert-Bu | F | 85 ± 20 | 1,200 ± 300 | 880 ± 67 |
| 1l | 4-Me | tert-Bu | Cl | 1.6 ± 0.5 | 107 ± 17 | 84 ± 20 |
| 1m | 4-Me | tert-Bu | Br | 2.9 ± 1.2 | 87 ± 17 | 93 ± 30 |
| 1n | 2,4,6-Me | tert-Bu | Br | 106 ± 16 | 1,340 ± 410 | 710 ± 150 |

[a] n ≥ 3. All compounds fully blocked U69,593 (>86%)

Notably, all the compounds of the present technology (1c to 1n) were significantly more potent than ML140 in inhibiting G protein function. The effect of changing from isopropyl to tert-butyl was even more pronounced, providing compounds possessing single-digit nanomolar potency. Halogen incorporation further improved the potency, resulting in the nearly equipotent fluoro analogue 1j, chloro analogue 1l, and the corresponding bromide 1m. While 2,4,6-trimethyl aryl sulfonamide substitution led to notably less potent compounds when compared to either the benzene sulfonamide, 4-methyl- or 4-ethyl-substituted aryl sulfonamide analogues of the present technology, such compounds are still more potent than ML140.

Table 2 provides the KOR recruitment of β arrestin 2 (percent response) toward a set concentration of the KOR agonist standard, U69,593.

TABLE 2

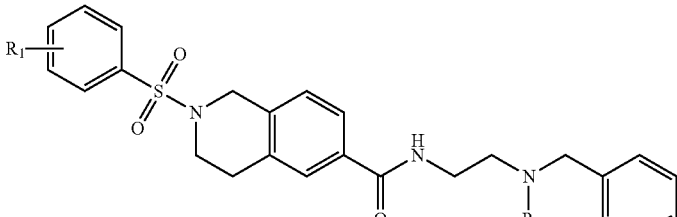

| entry/cmpd | R¹ | R² | R³ | β arrestin 2 Inhibition (% U69,593 Stimulation) | | |
|---|---|---|---|---|---|---|
| | | | | 1 µM | 100 nM | 10 nM |
| norBNI | — | — | — | 0.9 | 0.6 | 0.1 |
| 1b | 4-Me | tert-Bu | OMe | 0.0 | 0.8 | 0.0 |
| 1l | 4-Me | tert-Bu | Cl | 1.5 | 0.4 | 29.9 |

FIGS. 1A-D summarize the results of experiments comparing the detected concentrations of 11 (Example 26; referred to at AN4-015 in the Figure) or norBNI in the plasma and brain tissue of mice over the time period necessary for clearance (or up to 72 h) following a single 10 mg/kg IP dose in adult male C57Bl/6 mice according to methods discussed in Zhou, L.; Lovell, K. M.; Frankowski, K. J.; Slauson, S. R.; Phillips, A. M. Streicher, J. M.; Stahl, E.; Schmid, C. L.; Hodder, P.; Madoux, F.; Cameron, M. D.; Prisinzano, T. E.; Aubé, J.; Bohn, L. M. *J. Biol. Chem.* 2013, 288, 36703-36716. Briefly, test compounds were dissolved and delivered in 1:1:8 DMSO, Tween80, H$_2$O vehicle by IP injection. Plasma samples were collected at the times indicated from the same cohort of mice; brains were collected once at the times indicated. Plasma and brain were mixed with acetonitrile (1:5 v:v or 1:5 w:v, respectively) and the brains were disrupted via sonication. Following centrifugation at 16,000×g, the concentration of compound in the supernatant was determined using liquid chromatography (Shimadzu, Japan)/tandem mass spectrometry (AB Sciex, Franmingham, Mass.) operated in positive ion mode using multiple reaction monitoring methods. Separate standard curves were prepared in blank plasma and brain matrix. For brain, the concentration was calculated as amount of compound per mg tissue and converted to a concentration assuming a density of 1 wherein 1 g of tissue equals 1 ml.

Figure 1B:
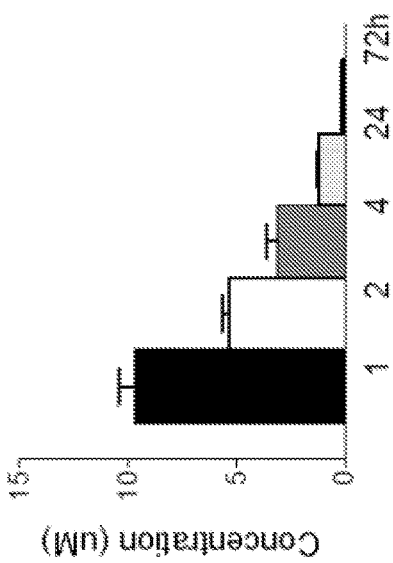
Figure 1C:
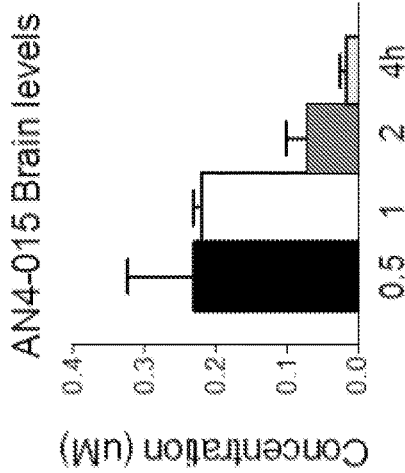
Figure 1D:
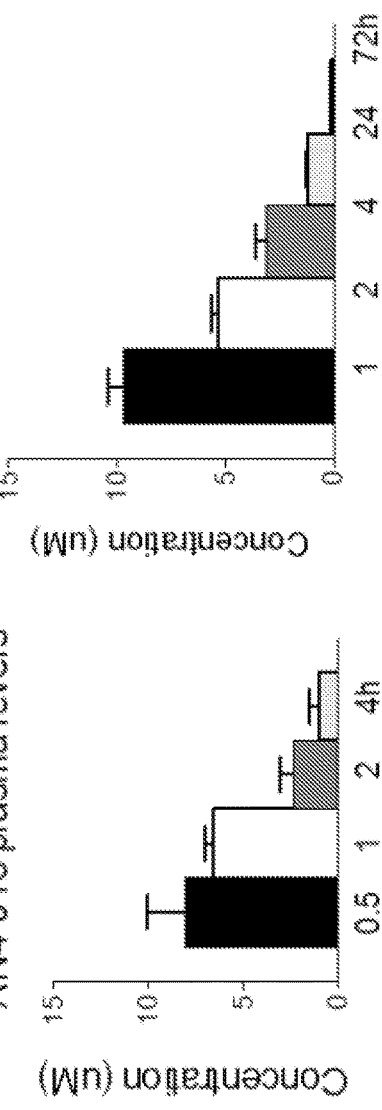

Compound 11 was found to cross the blood brain barrier into the CNS at concentrations similar to norBNI within 0.5 h (FIGS. 1A & 1B). Moreover, 11 was almost fully cleared from brain tissue by the 4 h measurement. In contrast, norBNI was still significantly present after 72 h. The plasma level measurements followed a similar though less striking pattern (FIGS. 1C & 1D). These experiments demonstrate three key attributes of the compounds of the present technology: (1) the ability to cross the blood brain barrier and access the CNS, (2) attain therapeutic concentrations in the brain tissue rapidly (within 1 h), and (3) the compounds of the present technology are steadily removed from both the plasma and brain. Such a pharmacokinetic profile illustrates the surprising and unexpected advantage of using compounds of the present technology as short-acting KOR antagonists.

Assessment of KOR Mediated Physiological Responses:

Compounds of the present technology will be tested, on their own and/or in combination with a known KOR agonist, to assess the modulation of physiological responses including: antinociception, locomotor activity, pruritis and alterations in reward thresholds.

1. Antinociception

Studies will be performed using mouse nociceptive assays including the warm water tail flick assay as known to those of ordinary skill in the art, such as discussed in Bohn L M, Lefkowitz R J, Caron M G. Differential mechanisms of morphine antinociceptive tolerance revealed in (beta)arrestin-2 knock-out mice. *J Neurosci.* 2002, 22(23):10494-500. Other tests of nociception include chemical-induced inflammatory pain and visceral pain, as exemplified in Tarselli M. A., et al. Synthesis of conolidine, a potent non-opiod analgesic for tonic and persistent pain. *Nat. Chem.* 2011, 3(6): 449-53. Antagonistic properties will be assessed by the compound's ability to block U50,488-induced antinociception. The structure of U50,488 is provided below.

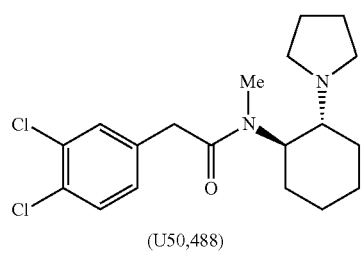 [SMILES: CN(C(=O)Cc1ccc(Cl)c(Cl)c1)[C@@H]1CCCC[C@H]1N1CCCC1]

(U50,488)

2. Antipruritic Effects

Antipruritic effects will be determined by pretreating mice with the KOR modulator (i.e., a compound of the present technology or a known KOR agonist). For agonists, this will be followed by a 40 mg/kg s.c. (nape of neck) injection of the pruritic agent, chloroquine phosphate and the number of scratching bouts in a 60 minute period will be counted, such as described in as previously described Morgenweck, J., Frankowski, K. J., Prisinzano, T. E., Aubé, J., Bohn, L. M. Investigation of the role of βarrestin2 in kappa opioid receptor modulation in a mouse model of pruritus. *Neuropharmacology*, 2015, 99:600-609. For suspected negative modulators, antagonism will be assessed by pretreating with a compound of the present technology, followed by KOR agonist (U50,488H) then the pruritic agent. It is expected the compounds of the present technology will block the antipruritic effect of U50,488 thus further demonstrating that the compounds of the present technology display antagonism towards nonbiased KOR agonists.

3. Locomotor Activity

Locomotor activity will be assessed by treating non-habituated mice (to reveal a measurable baseline activity as the reference KOR agonists will decrease activity) prior to placing in open field testing boxes (Versamax by Accuscan Instruments), such as described in Morgenweck, J. F. K., Prisinzano, T. E., Aubé, J., Bohn, L. M. Investigation of the role of βarrestin2 in kappa opioid receptor modulation in a mouse model of pruritus. *Neuropharmacology*, 2015, 99:600-609; Raehal, K. M., Schmid, C. L., Medvedev, I. O., Gainetdinov, R. R., Premont, R. T., Bohn, L. M. Morphine-induced physiological and behavioral responses in mice lacking G protein-coupled receptor kinase 6. Drug and alcohol dependence. 2009, 104(3):187-96; Bohn, L. M., Gainetdinov, R. R., Sotnikova, T. D., Medvedev, I. O., Lefkowitz, R. J., Dykstra, L. A., Caron, M. G. Enhanced rewarding properties of morphine, but not cocaine, in beta (arrestin)-2 knock-out mice. *The Journal of Neuroscience: the Official Journal of the Society for Neuroscience*, 2003, 23(32):10265-73; Medvedev, I. O., Gainetdinov, R. R., Sotnikova, T. D., Bohn, L. M., Caron, M. G., Dykstra, L. A. Characterization of conditioned place preference to cocaine in congenic dopamine transporter knockout female mice. *Psychopharmacology.* 2005; 180(3):408-13; and Bohn, L. M., Xu, F., Gainetdinov, R. R., Caron, M. G. Potentiated opioid analgesia in norepinephrine transporter knock-out mice. *The Journal of Neuroscience: the Official Journal of the Society for Neuroscience*, 2000, 20(24):9040-5.

Figure 2:
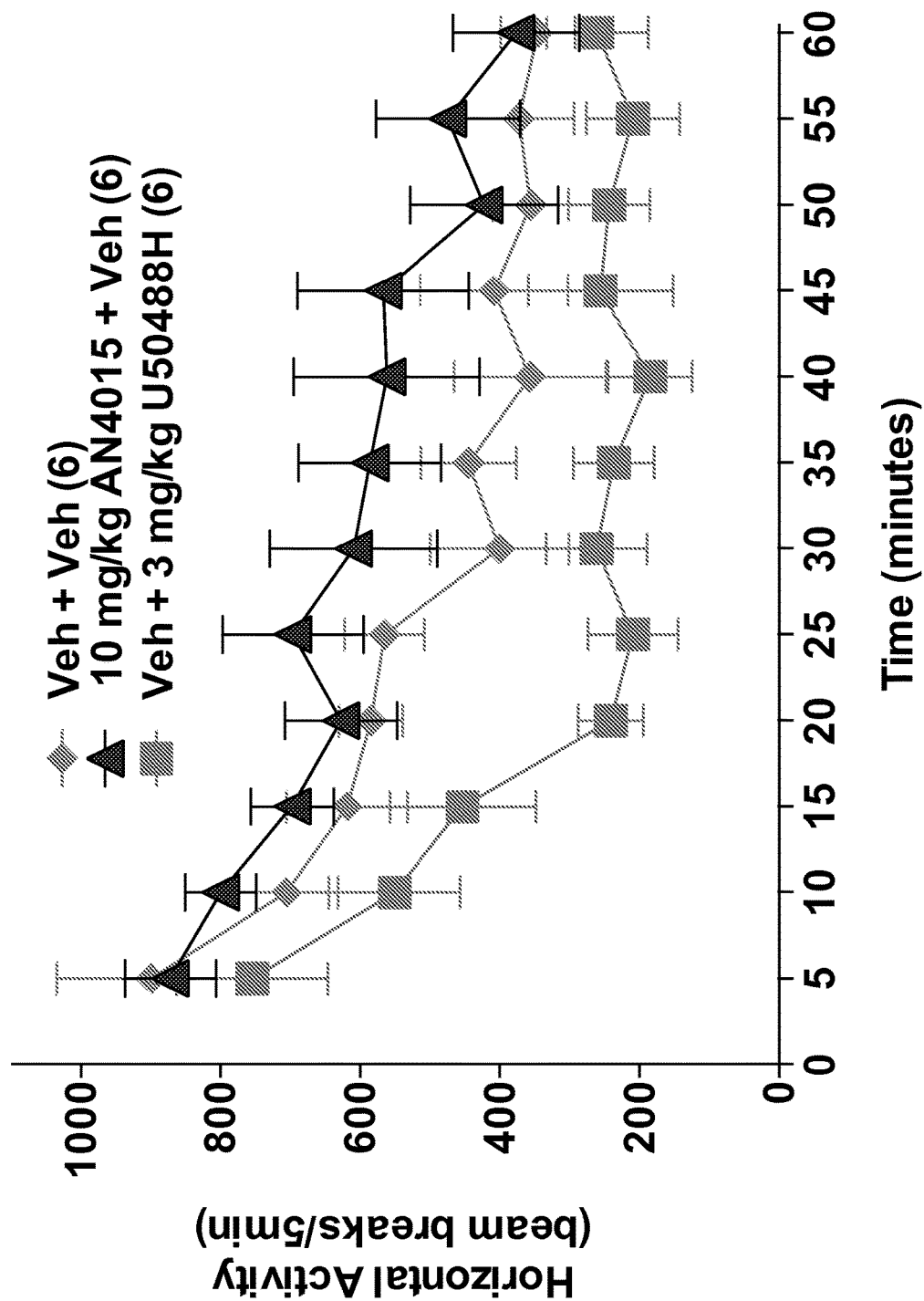
FIG. 2 shows the locomotor activity in mice for one embodiment of a compound of the present technology compared to known kappa opiod agonist U50, 488. The animal numbers are shown in parentheses.
Figure 3:
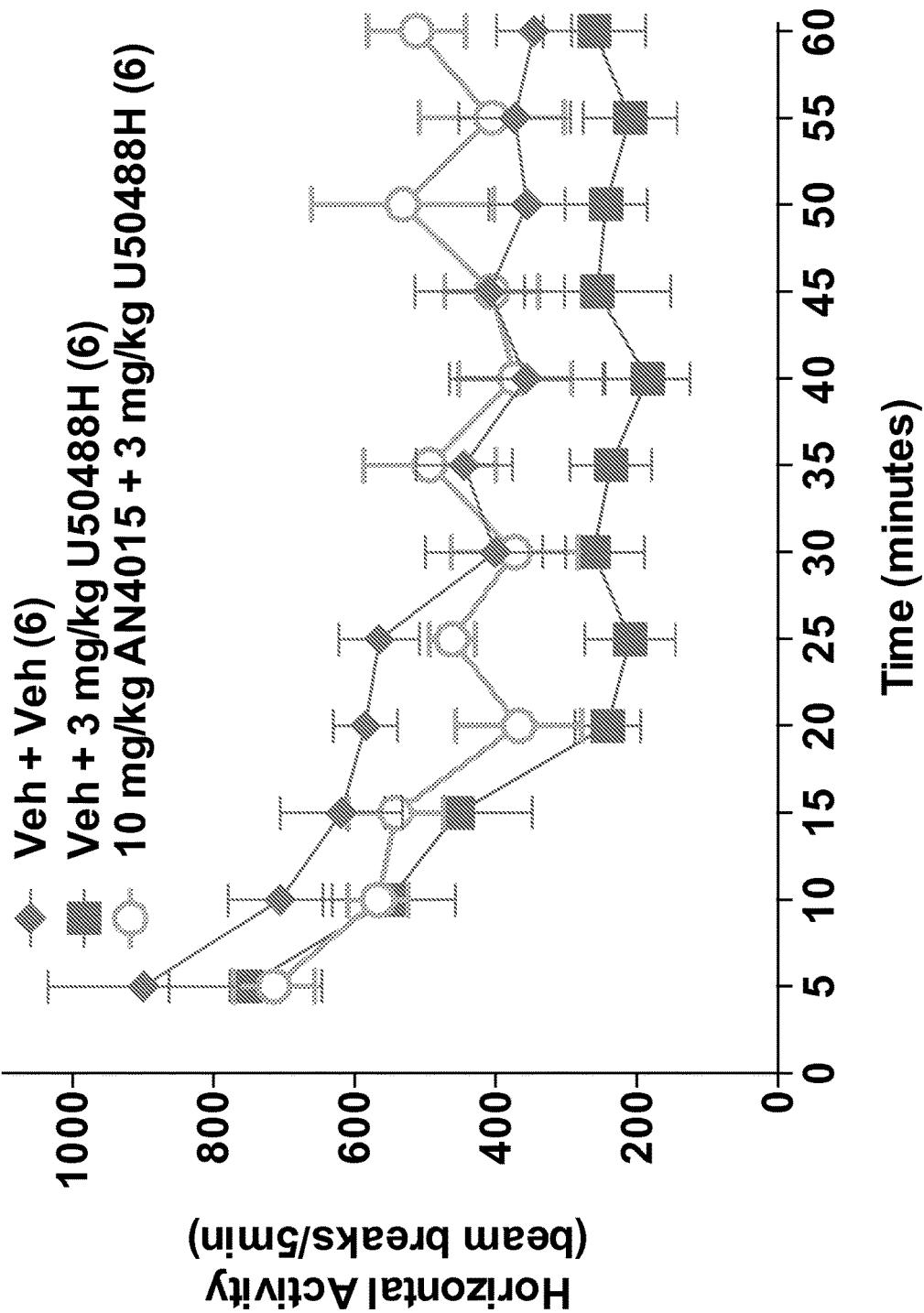
FIG. 3 shows the locomotor activity in mice pretreated with one embodiment of a compound of the present technology followed by treatment with U50,488 in comparison to mice that received a vehicle pretreatment followed by U50,488. The animal numbers are shown in parentheses.

For example, adult male C57BL/6 mice from Jackson Labs (~10 weeks old) were pretreated with either with vehicle (1:1:8, DMSO, Tween-80, dH$_2$O) or N-(2-((4-chlorobenzyl)(tert-butyl)amino)ethyl)-2-tosyl-1,2,3,4-tetrahydroisoquinoline-6-carboxamide (11 (Example 26) referred to at AN4015 in the Figure, 10 mg/kg, i.p.) and placed back in their home cage for 10 min. They were then treated with vehicle or U50,488 (10 l/g, s.c.) and placed in the open field activity box (Versascan Instruments) for immediate recordings. Ambulatory behavior was recorded for 1 hour in 5 minute bins via detection of infrared beam breaks. As shown in FIG. 2, Compound 11 was observed not to suppress activity compared to vehicle while U50, 488 does ($p<0.0001$, U50,488 vs. vehicle; Two-way ANOVA for drug effect). As illustrated in FIG. 3, a 10-minute pretreatment with Compound 11 (10 mg/kg) prevents the development of U50,488 hypolocomotion compared to mice that received a vehicle pretreatment followed by U50,488 ($p<0.0001$, Two-way ANOVA for Compound 11 effect vs. U50,488 treatment). The animal numbers are shown in parentheses in the legends of FIGS. 2 & 3.

4. Stress-Induced Reinstatement of Cocaine Conditioned Place Preference

Stress-induced reinstatement of cocaine conditioned place preference studies will be performed in C57Bl/6 mice, as discussed regarding optimized cocaine-induced CPP in this strain as well as in lines derived in part from this strain in Raehal, K. M., Schmid, C. L., Medvedev, I. O., Gainetdinov, R. R., Premont, R. T., Bohn, L. M. Morphine-induced physiological and behavioral responses in mice lacking G protein-coupled receptor kinase 6. *Drug Alcohol Depend.* 2009, 104(3): 187-96; Medvedev, I. O., Gainetdinov, R. R., Sotnikova, T. D., Bohn, L. M., Caron, M. G., Dykstra, L. A. Characterization of conditioned place preference to cocaine in congenic dopamine transporter knockout female mice. *Psychopharmacology (Berl).* 2005, 180(3):408-13; and Bohn, L. M., Gainetdinov, R. R., Sotnikova, T. D., Medvedev, I. O., Lefkowitz, R. J., Dykstra, L. A., Caron, M. G. Enhanced rewarding properties of morphine, but not cocaine, in beta(arrestin)-2 knock-out mice. *J Neurosci.* 2003, 23(32):10265-73. KOR antagonists have shown efficacious in preventing reinstatement in this line. A three department choice apparatus with ambient lighting, wall color and floor texture serving as conditioning cues. A non-biased approach will be taken and only mice that do not show preference during the preconditioning trials will be used. After cocaine preference is established, mice will be subjected to 7 days of daily saline injection of only saline paired with each side of the conditioning chamber, to extinguish the association of the paired chamber with the treatment of cocaine (10 mg/kg, i.p.). Extinction will be verified by the loss of preference between the two chambers. Twenty-four hours post-extinction, mice will be injected with compounds of the present technology (1-10 mg/kg, range determined based on PK and in vitro potency data) 20 minutes prior to being subjected to a stressor event (a 6 min cold water swim) and then placed immediately in the preference chambers. See Kreibich, A. S., Blendy, J. A. cAMP response element-binding protein is required for stress but not cocaine-induced reinstatement. *J Neurosci.* 2004, 24(30):6686-92. Demonstration of reinstatement will be an increase in time spent in the formerly cocaine paired side. U50,488 and/or Nor-BNI will serve as positive controls for each paradigm.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or

What is claimed is:
1. A compound according to formula I

I or stereoisomers, tautomers, solvates, and/or salts thereof;
wherein
$G^1$ and $G^2$ are each independently C=O or $S(O)_2$;
$R^1$, $R^2$, $R^3$, $R^4$, $R^5$, $R^7$, $R^8$, $R^9$, $R^{10}$, and $R^{11}$ are each independently H, halo, hydroxy, amino, cyano, trifluoromethyl, thiol, alkylthio, sulfoxide, sulfone, nitro, pentafluorosulfanyl, carboxylate, amide, ester, or a substituted or unsubstituted $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, or aryloyloxy group, where any two adjacent $R^1$, $R^2$, $R^3$, $R^4$, $R^5$, $R^7$, $R^8$, $R^9$, $R^{10}$, and $R^{11}$ may join to form a 5-membered or 6-membered substituted or unsubstituted heteroalkyl group;
$R^6$ is a branched $C_1$-$C_8$ alkyl group or a substituted or unsubstituted cycloalkyl or aryl group; and
$R^{12}$ and $R^{13}$ are each independently H or a substituted or unsubstituted $C_1$-$C_8$ alkyl or $C_5$-$C_7$ cycloalkyl group; and
n is 0, 1, or 2;
provided that when $G^1$ is $S(O)_2$, $G^2$ is C=O, $R^1$, $R^2$, $R^4$, $R^5$, $R^7$, $R^8$, $R^9$, $R^{10}$, $R^{11}$, $R^{12}$, $R^{13}$ are each H, $R^6$ is isopropyl, and n is 1, then $R^3$ is not methyl.

2. The compound of claim 1, wherein at least one of $R^1$, $R^2$, $R^3$, $R^4$, $R^5$, $R^7$, $R^8$, $R^9$, $R^{10}$, and $R^{11}$ is halo, hydroxy, cyano, trifluoromethyl, thiol, alkylthio, nitro, pentafluorosulfanyl, carboxylate, ester, or a substituted or unsubstituted $C_1$-$C_6$ alkyl, $C_1$-$C_6$ alkoxy, aryl, aryloxy, $C_1$-$C_6$ alkanoyl, $C_1$-$C_6$ alkanoyloxy, aryloyl, or aryloyloxy group.

3. The compound of claim 1, wherein at least one of $R^1$, $R^2$, $R^3$, $R^4$, $R^5$, $R^7$, $R^8$, $R^9$, $R^{10}$, and $R^{11}$ is hydroxy or a substituted or unsubstituted $C_1$-$C_6$ alkoxy or $C_1$-$C_6$ alkanoyloxy group.

4. The compound of claim 1, wherein at least one of $R^1$, $R^2$, $R^3$, $R^4$, $R^5$, $R^7$, $R^8$, $R^9$, $R^{10}$, and $R^{11}$ is hydroxy or an unsubstituted $C_1$-$C_6$ alkoxy group.

5. The compound of claim 1, wherein at least one of $R^1$, $R^2$, $R^3$, $R^4$, and $R^5$ is halo, hydroxy, carboxylate, ester, or a substituted or unsubstituted $C_1$-$C_6$ alkyl, $C_1$-$C_6$ alkoxy, $C_1$-$C_6$ alkanoyl, or $C_1$-$C_6$ alkanoyloxy group.

6. The compound of claim 1, wherein at least one of $R^7$, $R^8$, $R^9$, $R^{10}$, and $R^{11}$ is halo, hydroxy, cyano, trifluoromethyl, thiol, alkylthio, sulfoxide, sulfone, nitro, pentafluorosulfanyl, carboxylate, ester, or a substituted or unsubstituted $C_1$-$C_6$ alkyl, $C_1$-$C_6$ alkoxy, aryl, aryloxy, $C_1$-$C_6$ alkanoyl, $C_1$-$C_6$ alkanoyloxy, aryloyl, or aryloyloxy group.

7. The compound of claim 1, wherein at least one of $R^7$, $R^8$, $R^9$, $R^{10}$, and $R^{11}$ is hydroxy or an unsubstituted $C_1$-$C_6$ alkoxy group.

8. The compound of claim 1, wherein at least two of $R^1$, $R^2$, $R^3$, $R^4$, $R^5$, $R^7$, $R^8$, $R^9$, $R^{10}$, and $R^{11}$ are each independently halo, hydroxy, cyano, trifluoromethyl, nitro, pentafluorosulfanyl, carboxylate, ester, or a substituted or unsubstituted $C_1$-$C_6$ alkyl, $C_1$-$C_6$ alkoxy, aryl, aryloxy, $C_1$-$C_6$ alkanoyl, $C_1$-$C_6$ alkanoyloxy, aryloyl, or aryloyloxy group.

9. The compound of claim 1, wherein
$G^1$ is $S(O)_2$;
$G^2$ is C=O;
$R^1$, $R^4$, $R^5$, $R^7$, $R^{10}$, and $R^{11}$ are each H;
$R^2$, $R^3$, $R^8$, and $R^9$ are each independently halo, hydroxy, amino, cyano, trifluoromethyl, thiol, alkylthio, sulfoxide, sulfone, nitro, pentafluorosulfanyl, carboxylate, amide, ester, or a substituted or unsubstituted $C_1$-$C_6$ alkyl, $C_1$-$C_6$ alkoxy, aryl, aryloxy, $C_1$-$C_6$ alkanoyl, $C_1$-$C_8$ alkanoyloxy, aryloyl, or aryloyloxy group, where any two adjacent $R^2$, $R^3$, $R^8$, and $R^9$ may join to form a 5-membered or 6-membered substituted or unsubstituted heteroalkyl group;
$R^6$ is a branched $C_1$-$C_8$ alkyl group;
$R^{12}$ and $R^{13}$ are each H; and
n is 1.

10. The compound of claim 1, wherein
$G^1$ is $S(O)_2$;
$G^2$ is C=O;
$R^1$, $R^4$, $R^5$, $R^7$, $R^{10}$, and $R^{11}$ are each H;
one of $R^2$ and $R^3$ is halo, hydroxy, or a unsubstituted $C_1$-$C_6$ alkyl, $C_1$-$C_6$ alkoxy, $C_1$-$C_6$ alkanoyl, or $C_1$-$C_8$ alkanoyloxy group and the other $R^2$ or $R^3$ is H;
one of $R^8$ and $R^9$ is halo, hydroxy, amino, cyano, trifluoromethyl, thiol, alkylthio, sulfoxide, sulfone, nitro, pentafluorosulfanyl, carboxylate, amide, ester, or a substituted or unsubstituted $C_1$-$C_6$ alkoxy, $C_1$-$C_6$ alkanoyl, or $C_1$-$C_8$ alkanoyloxy group, and the other $R^8$ or $R^9$ is H;
$R^6$ is a branched $C_1$-$C_8$ alkyl group;
$R^{12}$ and $R^{13}$ are each H; and
n is 1.

11. The compound of claim 1, wherein $R^6$ is a branched $C_1$-$C_8$ alkyl group or a substituted or unsubstituted cycloalkyl group.

12. The compound of claim 1, wherein $R^6$ is isopropyl, sec-butyl, tert-butyl, isopentyl, neopentyl, or adamantyl.

13. The compound of claim 1, wherein $R^6$ is tert-butyl, neopentyl, or adamantyl.

14. The compound of claim 1, wherein the compound is selected from the group consisting of

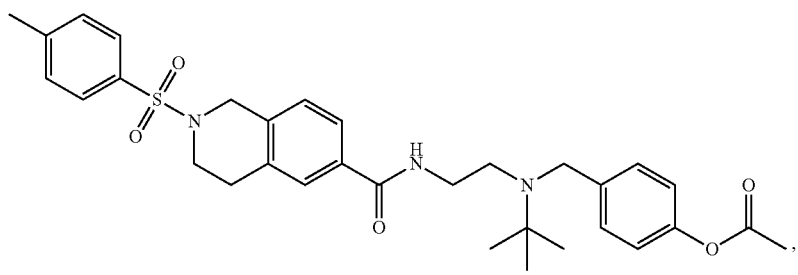
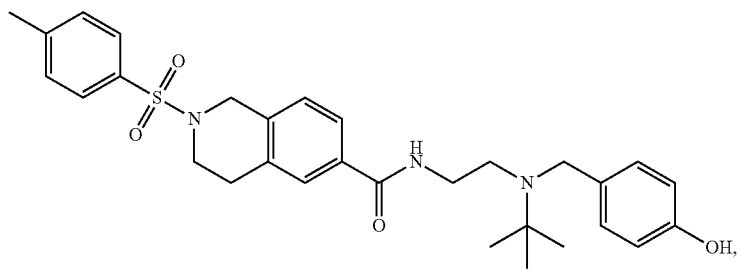
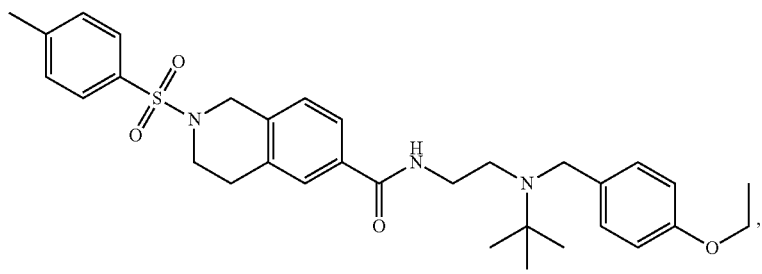
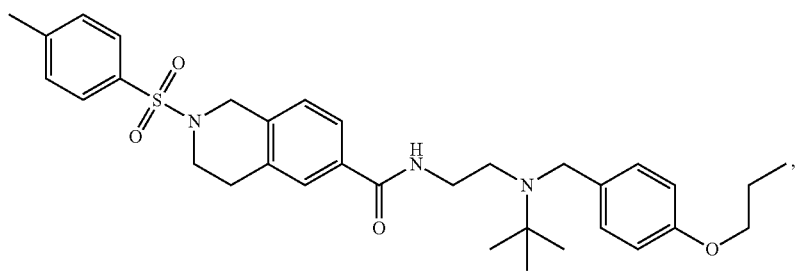
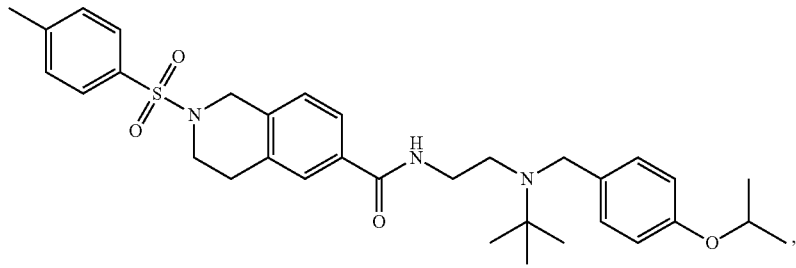
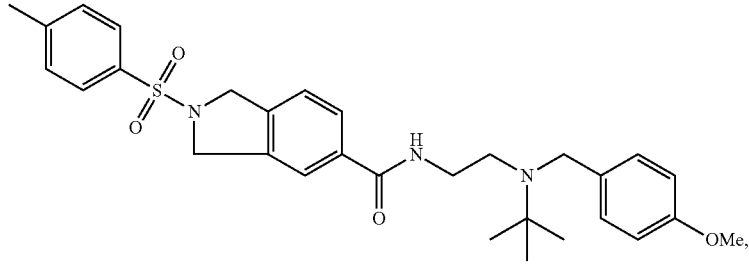

-continued
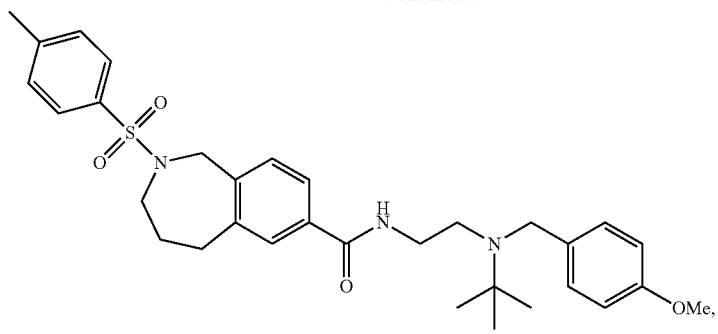
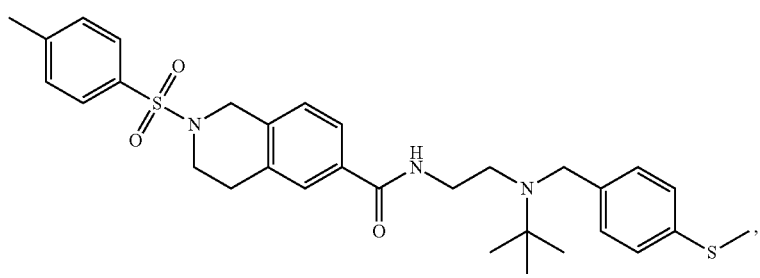
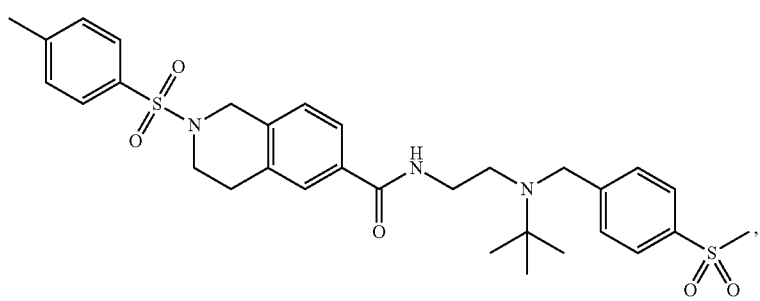
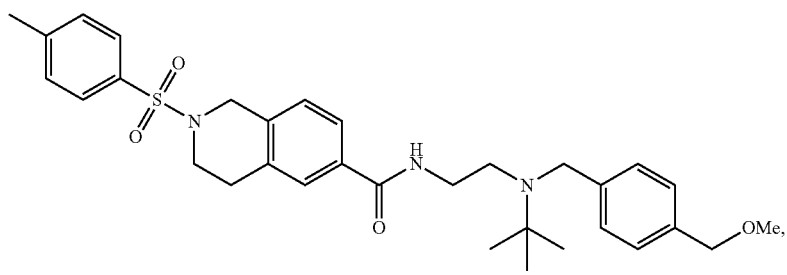
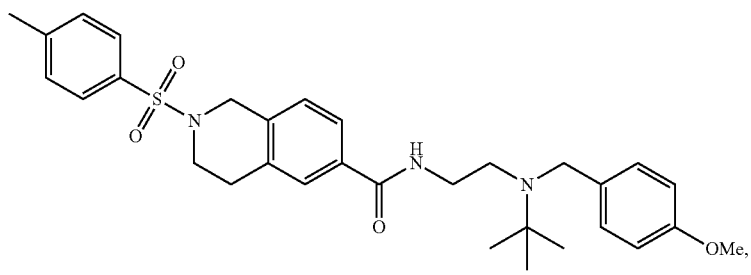
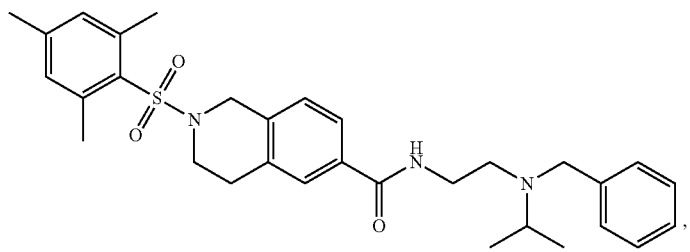

-continued
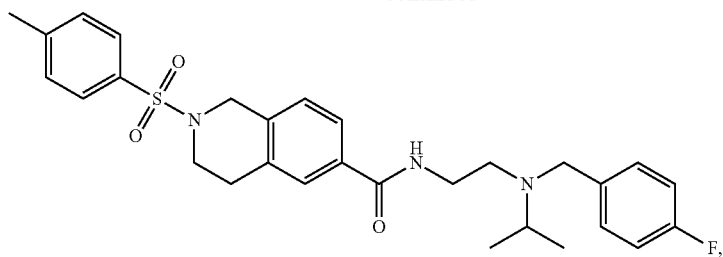
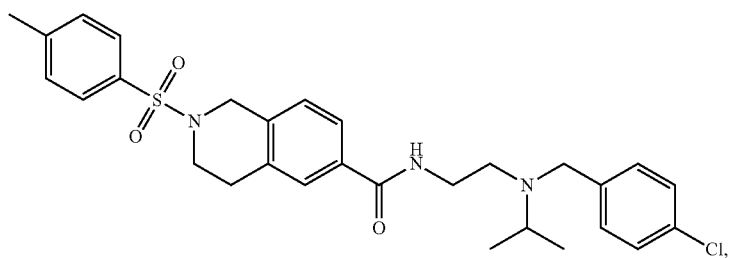
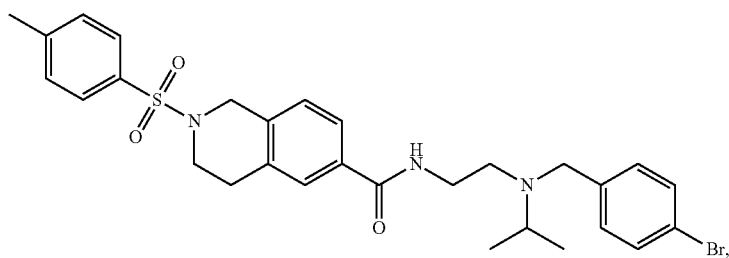
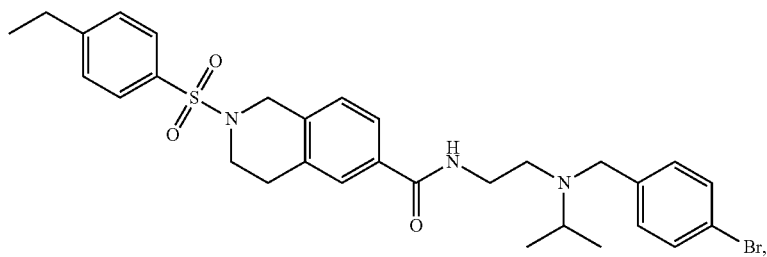
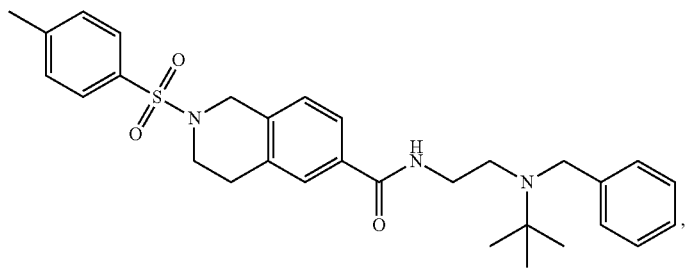
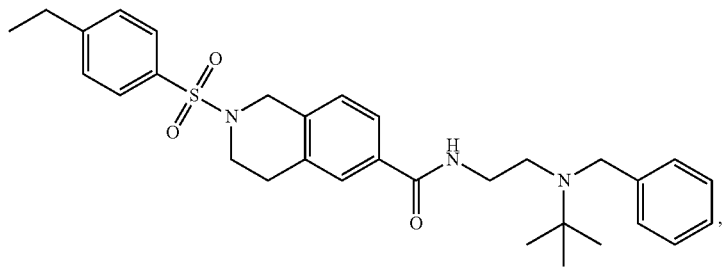

-continued
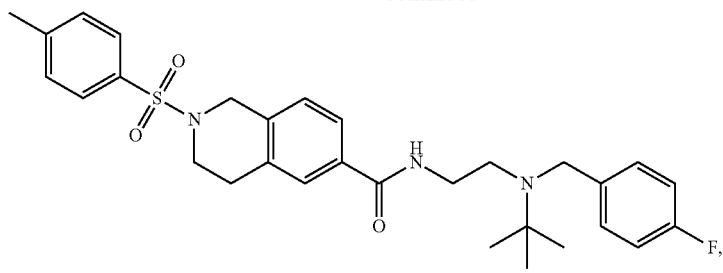
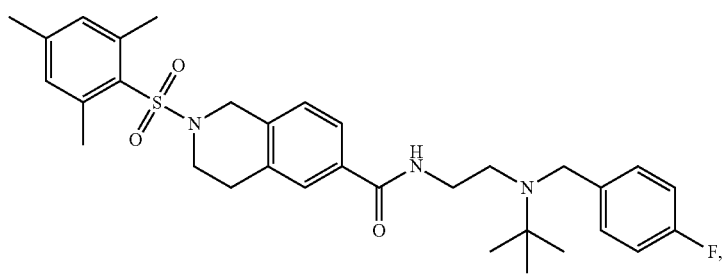
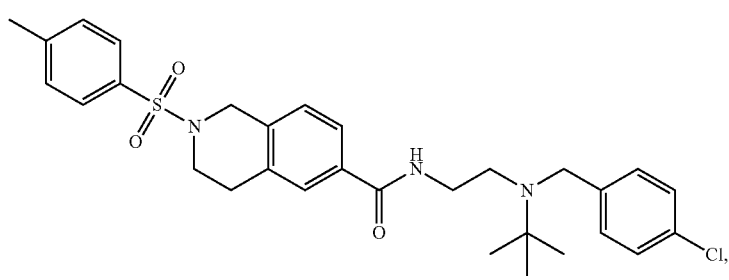
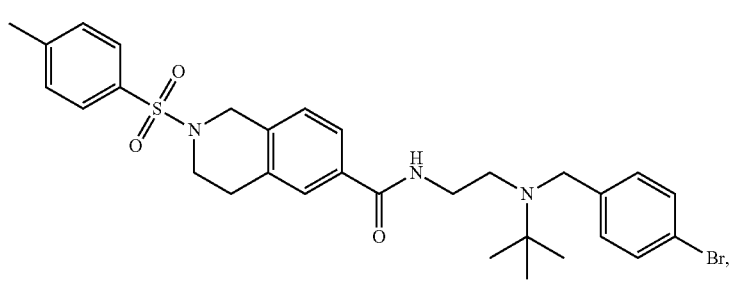
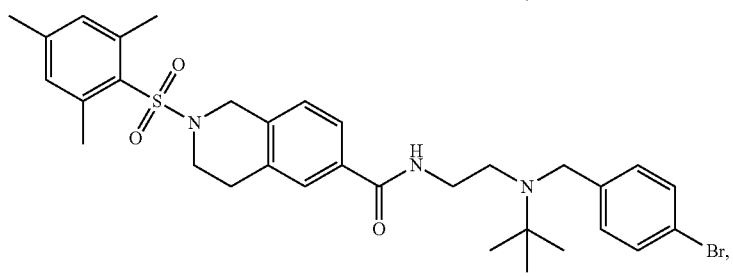
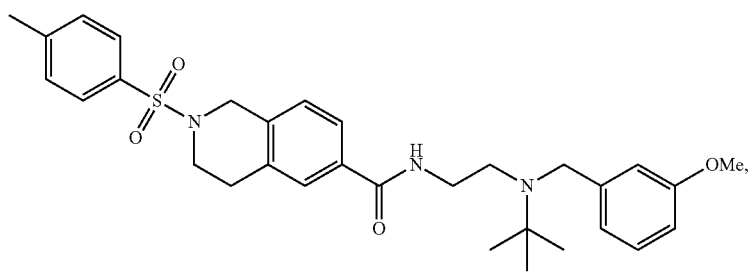

-continued
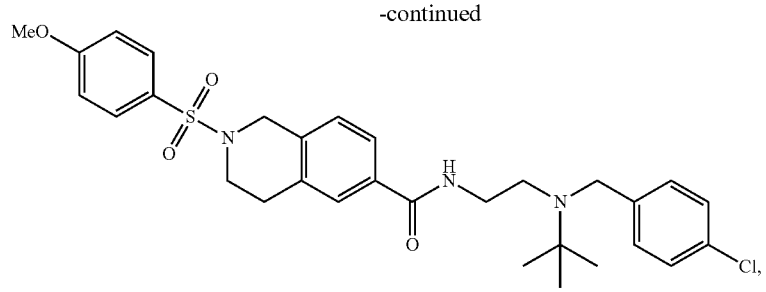
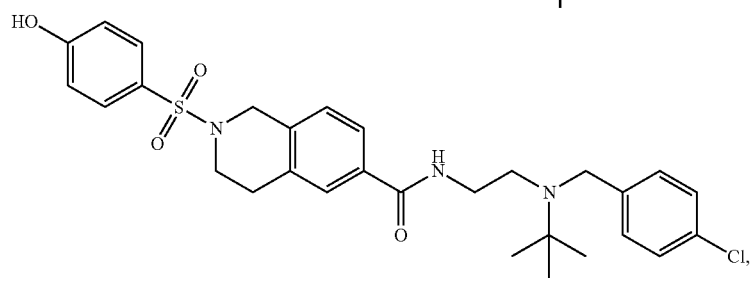
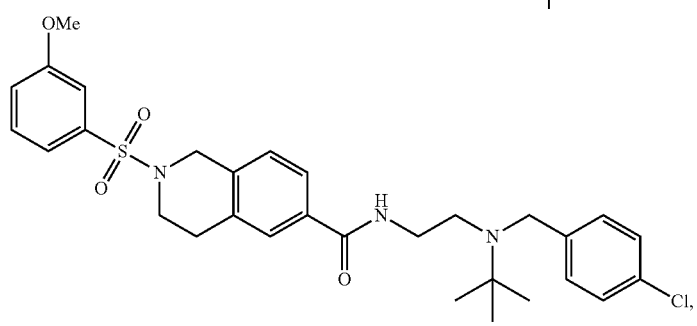
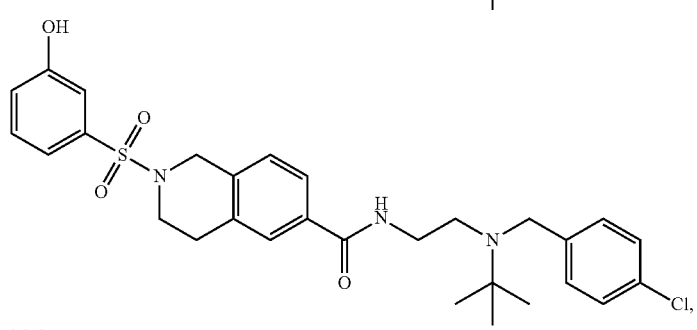
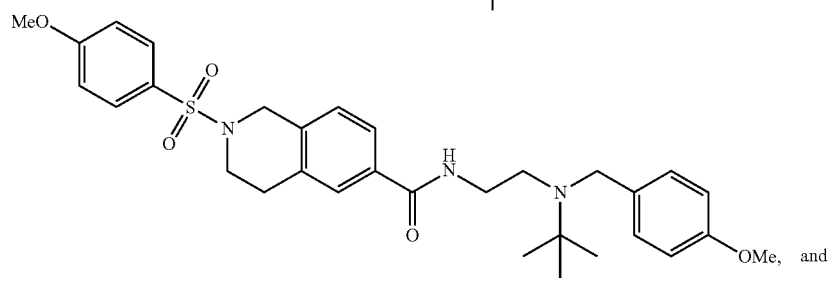
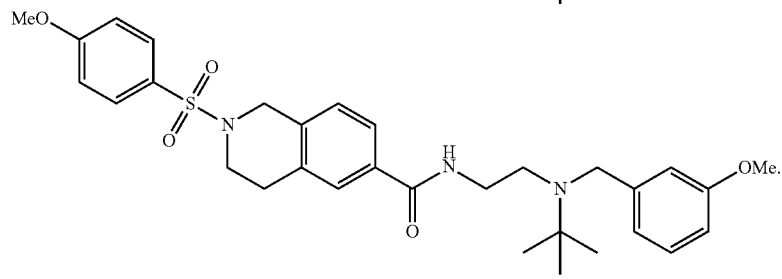

15. A composition comprising the compound of claim 1 and a pharmaceutically acceptable carrier.

16. A method comprising inhibiting β-arrestin recruitment in a subject by administering an effective amount of a compound of claim 1.

17. The method of claim 16, wherein the subject is suffering from depression, alcohol addiction, or cocaine addiction.

18. A method of inhibiting β-arrestin recruitment wherein the method comprises contacting a kappa opioid receptor with a compound of claim 1.

* * * * *